(12) United States Patent
Conway et al.

(10) Patent No.: US 9,408,871 B2
(45) Date of Patent: Aug. 9, 2016

(54) METHODS FOR INHIBITING COMPLEMENT ACTIVATION AND USES THEREOF

(71) Applicant: THE UNIVERSITY OF BRITISH COLUMBIA, Vancouver (CA)

(72) Inventors: Edward Conway, Vancouver (CA); Jing Zhao Cui, Vancouver (CA); Jonathan Foley, Vancouver (CA); Michael Krisinger, Vancouver (CA); Joanne Matsubara, Vancouver (CA); Linnette Ocariza, Vancouver (CA); Jovian Wat, Burnaby (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 0 days.

(21) Appl. No.: 14/536,520

(22) Filed: Nov. 7, 2014

(65) Prior Publication Data
US 2015/0132403 A1    May 14, 2015

Related U.S. Application Data

(60) Provisional application No. 61/901,759, filed on Nov. 8, 2013.

(51) Int. Cl.
| | | |
|---|---|---|
| *A61K 31/66* | (2006.01) | |
| *A61K 33/42* | (2006.01) | |
| *A01N 59/26* | (2006.01) | |
| *A01N 1/02* | (2006.01) | |
| *G01N 33/53* | (2006.01) | |

(52) U.S. Cl.
CPC .............. *A61K 33/42* (2013.01); *A01N 1/0226* (2013.01); *A01N 59/26* (2013.01); *G01N 33/5308* (2013.01)

(58) Field of Classification Search
CPC ...................................................... A61K 31/66
See application file for complete search history.

(56) References Cited

U.S. PATENT DOCUMENTS

| 6,537,589 | B1 * | 3/2003 | Chae et al. ............... 424/602 |
| 2006/0198837 | A1 * | 9/2006 | Morrissey et al. ......... 424/94.64 |
| 2009/0110750 | A1 * | 4/2009 | Greener ................... 424/618 |
| 2010/0106243 | A1 * | 4/2010 | Wittchow ................. 623/1.42 |
| 2010/0166862 | A1 * | 7/2010 | Francois et al. ............ 424/484 |
| 2010/0262229 | A1 * | 10/2010 | Rohde .................... 623/1.46 |
| 2010/0284998 | A1 * | 11/2010 | Smith et al. .............. 424/94.64 |

FOREIGN PATENT DOCUMENTS

WO    WO 2012101218 A1 *  8/2012

OTHER PUBLICATIONS

Makrides (1998). "Therapeutic Inhibition of the Complement System." Pharmacological Reviews, 50(1): 59-87.*
Bae JS, Lee W, Rezaie AR. Polyphosphate elicits proinflammatory responses that are counteracted by activated protein C in both cellular and animal models. J Thromb Haemost. 2012; 10(6):1145-1151.
Bae JS, et al. Concentration dependent dual effect of thrombin in endothelial cells via Par-1 and Pi3 Kinase. J Cell Physiol. 2009; 219(3):744-751.
Beinrohr L, et al. Serpins and the complement system. Methods in enzymology. 2011; 499: 55-75.
Bos IG, Hack CE, Abrahams JP. Structural and functional aspects of C1-inhibitor. Immunobiology. 2002; 205: 518-33.
Brown MR, Kornberg A. Inorganic polyphosphate in the origin and survival of species. Proc Natl Acad Sci USA. 2004; 101(46):16085-16087.
Brown MR, Kornberg A. The long and short of it-polyphosphate, PPK and bacterial survival. Trends Biochem Sci. 2008; 33(6):284-290.
Caen J, Wu Q. Hageman factor, platelets and polyphosphates: early history and recent connection. J Thromb Haemost . 2010; 8(8):1670-1674.
Del Conde I, et al. Platelet activation leads to activation and propagation of the complement system. J Exp Med. 2005; 201(6):871-879.
Delvaeye M, Conway EM. Coagulation and innate immune responses: can we view them separately? Blood. 2009; 114(2):2367-2374.
Di Cera E. Thrombin as procoagulant and anticoagulant. J Thromb Haemost. 2007; 5 Suppl 1:196-202.
Docampo R, Moreno SN. Acidocalcisomes. Cell Calcium. 2011; 50(2):113-119.
Drake WT, et al. Thrombin enhancement of interleukin-1 and tumor necrosis factor-alpha induced polymorphonuclear leukocyte migration. Lab Invest. 1992; 67(5):617-627.

(Continued)

*Primary Examiner* — Gollamudi Kishore
*Assistant Examiner* — Amanda Heyes

(57) ABSTRACT

The present invention provides methods for inhibiting complement activation and uses thereof. More specifically, the present invention provides methods for inhibiting complement activation using inorganic polyphosphates of at least 10 phosphate units. The polyphosphates inhibit complement activation by one or more of: binding to the C6 complement protein, C1-esterase inhibitor (C1-inh), factor H or factor B; enhancing the activity of C1-inh; interfering with C1s-mediated cleavage of C2; destabilizing the C5b-6 complement protein complex; interfering with C5b,6 interaction with C7; interfering with binding of C5b-7 to a cell membrane; interfering with integration of C5b-7 into a cell membrane; interfering with binding of C5b-8 to a cell membrane; interfering with integration of C5b-8 into a cell membrane; destabilizing the membrane attack complex (MAC); or reducing the amount of C5b-9 deposited on a cell surface.

6 Claims, 21 Drawing Sheets

(56) References Cited

OTHER PUBLICATIONS

Du S, et al. Decorin inhibits angiogenic potential of choroid-retinal endothelial cells by downregulating hypoxia-induced Met, Rac1, HIF-1alpha and VEGF expression in cocultured retinal pigment epithelial cells. Experimental eye research 2013; 116: 151-60.
Dunn KC, et al. ARPE-19, a human retinal pigment epithelial cell line with differentiated properties. Experimental eye research. 1996; 62: 155-69.
Falgarone G, Chiocchia G. Chapter 8: Clusterin: A multifacet protein at the crossroad of inflammation and autoimmunity. Adv Cancer Res. 2009; 104:139-170.
Fujita T, et al. Thrombin enhances the production of monocyte chemoattractant protein-1 and macrophage inflammatory protein-2 in cultured rat glomerular epithelial cells. Nephrol Dial Transplant. 2008; 23(11):3412-3417.
Girardi G, Mackman N. Tissue factor in antiphospholipid antibody-induced pregnancy loss: a pro-inflammatory molecule. Lupus. 2008; 17(10):931-936.
Gunay-Aygun M, Huizing M, Gahl WA. Molecular defects that affect platelet dense granules. Semin Thromb Hemost. 2004; 30(5):537-547.
Hadders MA, et al. Assembly and regulation of the membrane attack complex based on structures of C5b6 and sC5b9. Cell Rep. 2012; 1(3):200-207.
Harold FM. Inorganic polyphosphates in biology: structure, metabolism, and function. Bacteriol Rev. 1966; 30 (4):772-794.
Hobart MJ, et al. Difficulties in the ascertainment of C9 deficiency: lessons to be drawn from a compound heterozygote C9-deficient subject. Clin Exp Immunol. 1997; 108(3):500-506.
Huber-Lang M, et al. Generation of C5a in the absence of C3: a new complement activation pathway. Nat Med. 2006; 12(6):682-687.
Hurford MT, Sebastiano C. Hermansky-pudlak syndrome: report of a case and review of the literature. Int J Clin Exp Pathol. 2008; 1(6):550-554.
Jessen TE, Barkholt V, Welinder KG. A simple alternative pathway for hemolytic assay of human complement component C3 using methylamine-treated plasma. J Immunol Methods. 1983; 60(1-2):89-100.
Kaplan J, De Domenico I, Ward DM. Chediak-Higashi syndrome. Curr Opin Hematol. 2008; 15(1):22-29.
Kimura A, Ikeo K, Nonaka M. Evolutionary origin of the vertebrate blood complement and coagulation systems inferred from liver EST analysis of lamprey. Dev Comp Immunol. 2009; 33(1):77-87.
Kornberg A, Rao NN, Ault-Riche D. Inorganic polyphosphate: a molecule of many functions. Annu Rev Biochem. 1999; 68:89-125.
Krarup A, et al. Simultaneous activation of complement and coagulation by MBL-associated serine protease 2. PLoS ONE. 2007; 2(7):e623.
Krisinger MJ, et al. Thrombin generates previously unidentified C5 products that support the terminal complement activation pathway. Blood. 2012; 120(8):1717-1725.
La Bonte L R, et al. Mannose-binding lectin-associated serine protease-1 is a significant contributor to coagulation in a murine model of occlusive thrombosis. J Immunol. 2012; 188(2):885-891.
Lachmann PJ, Thompson RA. Reactive lysis: the complement-mediated lysis of unsensitized cells. II. The characterization of activated reactor as C56 and the participation of C8 and C9. J Exp Med. 1970; 131(4):643-657.
Lechtenberg BC, Freund SM, Huntington JA. An ensemble view of thrombin allostery. Biol Chem. 2012; 393(9):889-898.
Licht C, et al. Platelet-associated complement factor H in healthy persons and patients with atypical HUS. Blood. 2009; 114(20):4538-4545.
Lorenz B, et al. Anti-HIV-1 activity of inorganic polyphosphates. J Acquir Immune Defic Syndr Hum Retrovirol. 1997; 14(2):110-118.
Lorenz B, Schroder HC. Mammalian intestinal alkaline phosphatase acts as highly active exopolyphosphatase. Biochim Biophys Acta. 2001; 1547(2):254-261.
Luyendyk JP, et al. Tissue factor-deficiency and protease activated receptor-1-deficiency reduce inflammation elicited by diet-induced steatohepatitis in mice. Am J Pathol. 2010; 176(1):177-186.
Morgan BP. The complement system: an overview. Methods Mol Biol. 2000; 150:61-71.
Morser J. Thrombomodulin links coagulation to inflammation and immunity. Curr Drug Targets. 2012; 13(3):421-431.
Muller F, et al. Platelet polyphosphates are proinflammatory and procoagulant mediators in vivo. Cell. 2009; 139(6):1143-1156.
Muller F, Renne T. Platelet polyphosphates: the nexus of primary and secondary hemostasis. Scand J Clin Lab Invest. 2011; 71(2):82-86.
Murray-Rust TA, et al. Modulation of the proteolytic activity of the complement protease C1s by polyanions: implications for polyanion-mediated acceleration of interaction between C1s and SERPING1. Biochem J. 2009; 422:295-303.
Mutch NJ, et al. Polyphosphate binds with high affinity to exosite II of thrombin. J Thromb Haemost. 2010; 8(3):548-555.
Mutch NJ, et al. Polyphosphate modifies the fibrin network and down-regulates fibrinolysis by attenuating binding of tPA and plasminogen to fibrin. Blood. 2010; 115(19):3980-3988.
Niesen FH, Berglund H, Vedadi M. The use of differential scanning fluorimetry to detect ligand interactions that promote protein stability. Nat Protoc. 2007; 2(9):2212-2221.
Ninomiya H, Sims PJ. The human complement regulatory protein CD59 binds to the alpha-chain of C8 and to the "b" domain of C9. J Biol Chem. 1992; 267(19):13675-13680.
Nurden A, Nurden P. Advances in our understanding of the molecular basis of disorders of platelet function. J Thromb Haemost. 2011; 9 Suppl 1:76-91.
Oehmcke S, Herwald H. Contact system activation in severe infectious diseases. J Mol Med. 2010; 88(2 ):121-126.
Podack ER, Kolb WP, Muller-Eberhard HJ. The SC5b-7 complex: formation, isolation, properties, and subunit composition. J Immunol. 1977; 119(6):2024-2029.
Rao NN, Kornberg A. Inorganic polyphosphate regulates responses of *Escherichia coli* to nutritional stringencies, environmental stresses and survival in the stationary phase. Prog Mol Subcell Biol. 1999; 23:183-195.
Rawal N, Pangburn MK. C5 convertase of the alternative pathway of complement. Kinetic analysis of the free and surface-bound forms of the enzyme. J Biol Chem. 1998; 273(27):16828-16835.
Rezaie AR. Regulation of the Protein C Anticoagulant and Antiinflammatory Pathways. Curr. Med Chem 2010; 17(19) 2059-2069.
Ricklin D, Lambris JD. Complement-targeted therapeutics. Nat Biotechnol. 2007; 25(11):1265-1275.
Risitano AM. Paroxysmal nocturnal hemoglobinuria and the complement system: recent insights and novel anticomplement strategies, Adv Exp Med Biol. 2013; 735:155-172.
Rondina MT, Weyrich AS, Zimmerman GA. Platelets as celllular effectors of inflammation in vascular diseases. Circ Res. 2013; 112(11):1506-1519.
Ruiz FA, et al. Human platelet dense granules contain polyphosphate and are similar to acidocalcisomes of bacteria and unicellular eukaryotes. J Biol Chem. 2004; 279(43):44250-44257.
Schmaier AH, et al. Expression of platelet 1 inhibitor. Blood. 1993; 82(2):465-474.
Smith SA, et al. Polyphosphate exerts differential effects on blood clotting, depending on polymer size. Blood. 2010; 116(20):4353-4359.
Smith SA, et al. Polyphosphate modulates blood coagulation and fibrinolysis. Proc Natl Acad Sci USA. 2006; 103 (4):903-908.
Smith SA, Morrissey JH. Polyphosphate as a general procoagulant agent. J Thromb Haemost, 2008; 6(10):1750-1756.
Smith SA, Morrissey JH. Polyphosphate enhances fibrin clot structure. Blood. 2008; 112(7):2810-2816.
Smith SA, Morrissey JH. Sensitive fluorescence detection of polyphosphate in polyacrylamide gels using 4',6-diamidino-2-phenylindol. Electrophoresis. 2007; 28(19):3461-3465.
Takahashi K, et al. Mannose-binding lectin and its associated proteases (MASPs) mediate coagulation and its deficiency is a risk

(56) References Cited

OTHER PUBLICATIONS factor in developing complications from infection, including disseminated intravascular coagulation. Immunobiology. 2011; 216(1-2):96-102.

Tinsley CR, Gotschlich EC. Cloning and characterization of the meningococcal polyphosphate kinase gene: production of polyphosphate synthesis mutants. Infect Immun. 1995; 63(5):1624-1630.

Tschopp J, et al. Clusterin, the human apolipoprotein and complement inhibitor, binds to complement C7, C8 beta, and the b domain of C9. J Immunol. 1993; 151(4):2159-2165.

Van Den Berg CW, Morgan BP. Complement-inhibiting activities of human CD59 and analogues from rat, sheep, and pig are not homologously restricted. J Immunol. 1994; 152(8):4095-4101.

Van Der Meijden PE, Heemskerk JW. Polyphosphates: a link between platelet activation, intrinsic coagulation and inflammation? Expert Rev Hematol. 2010; 3(3):269-272.

Wadgaonkar R, Somnay K, Garcia JG. Thrombin induced secretion of macrophage migration inhibitory factor (MIF) and its effect on nuclear signaling in endothelium. J Cell Biochem. 2008; 105(5):1279-1288.

Wat J, et al. Polyphosphate suppresses complement via the terminal pathway. Blood. 2014; 123: 768-76.

Weiler H. Regulation of inflammation by the protein C system. Crit Care Med. 2010; 38(2 Suppl):S18-25.

Wiedmer T, Esmon CT, Sims PJ. Complement proteins C5b-9 stimulate procoagulant activity through platelet prothrombinase. Blood. 1986; 68(4):875-880.

Xu J, Lupu F, Esmon CT. Inflammation, innate immunity and blood coagulation. Hamostaseologie. 2010; 30(1):5-6, 8-9.

Yin W, Ghebrehiwet B. Peerschke EI. Expression of complement components and inhibitors on platelet microparticles. Platelets. 2008; 19(3):225-233.

Zeerleder S. C1-inhibitor: more than a serine protease inhibitor. Semin Thromb Hemost. 2011; 37(4)362-374.

Zhang Q, Li Y, Tang CM. The role of the exopolyphosphatase PPX in avoidance by Neisseria meningitidis of complement-mediated killing. J Biol Chem. 2010; 285(44):34259-34268.

Elvin Abraham Kabat & Manfred Martin Mayer, Complement and Complement Fixation, Experimental Immunochemistry, 2nd ed, (Springfield: CC Thomas, 1961) at 135-240.

Wat J, Polyphosphates as modulators of complement activation. UBC Experimental Medicine Student Research Day Nov. 16, 2012, Vancouver, B.C.

* cited by examiner

FIGURE 5A
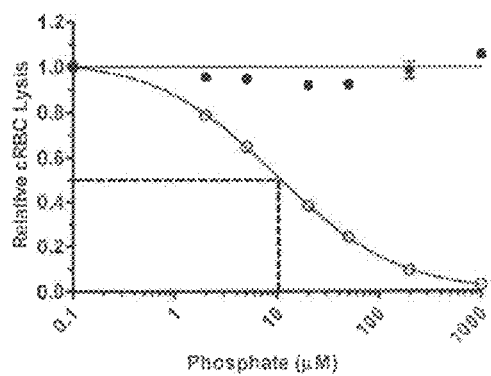
FIGURE 5B
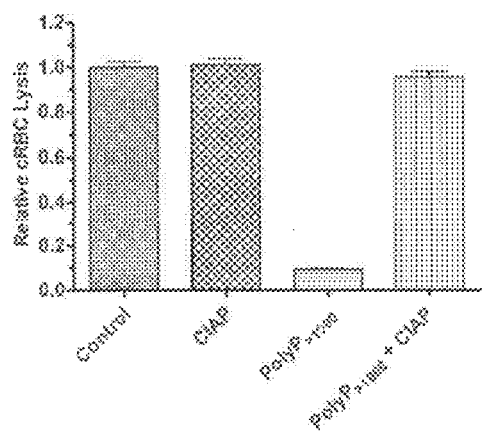
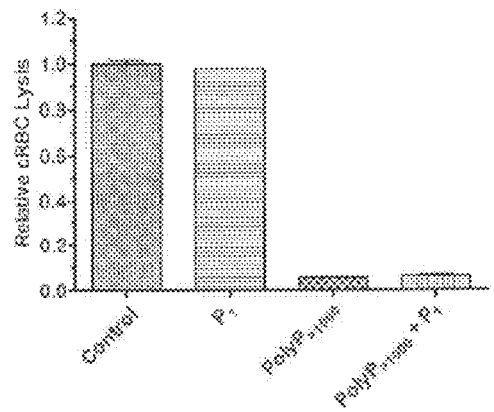
FIGURE 5C

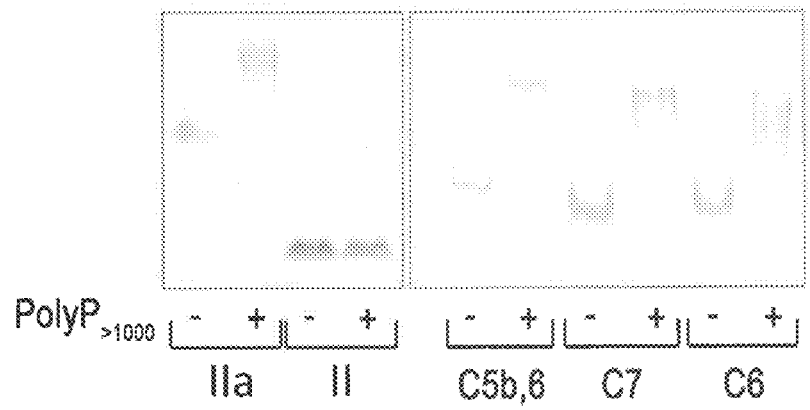
FIGURE 9
FIGURE 10A
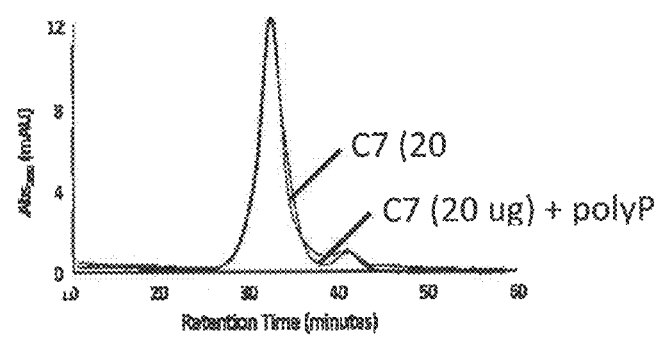
FIGURE 10B
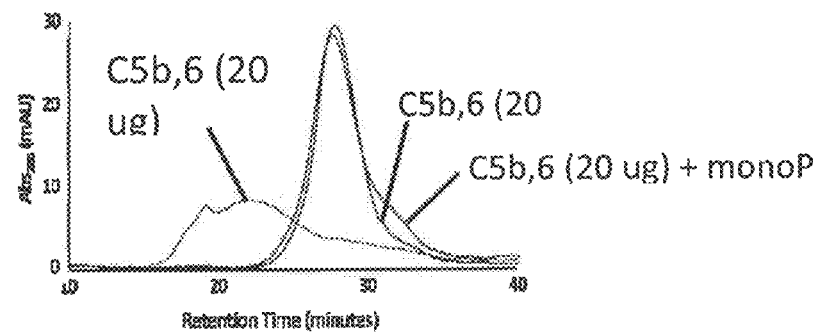

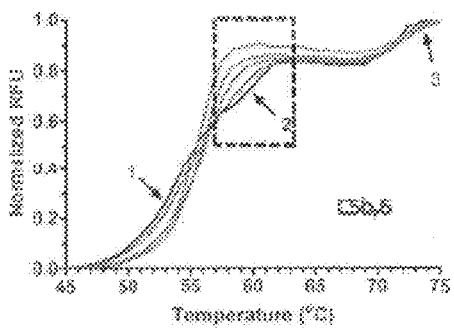
FIGURE 11A
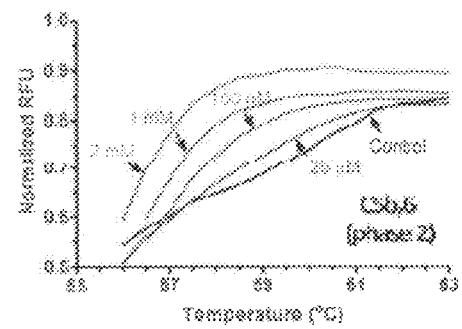
FIGURE 11B
FIGURE 11C
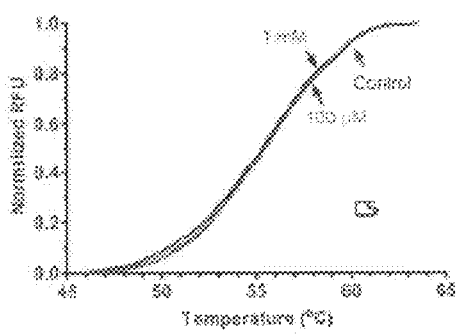
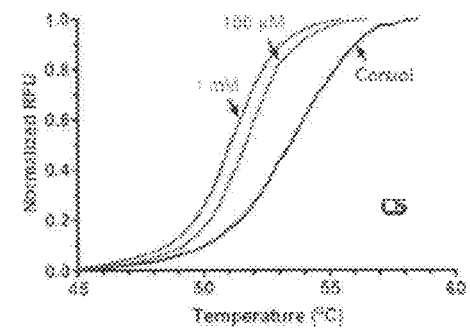
FIGURE 11D
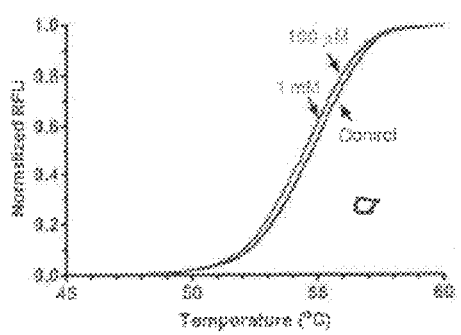
FIGURE 11E FIGURE 13A
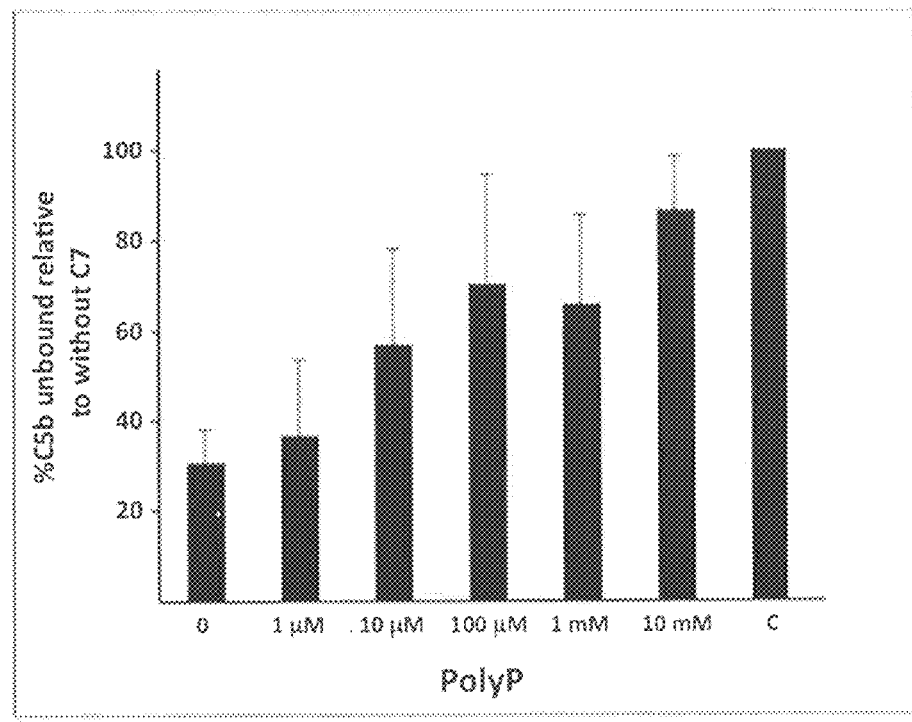
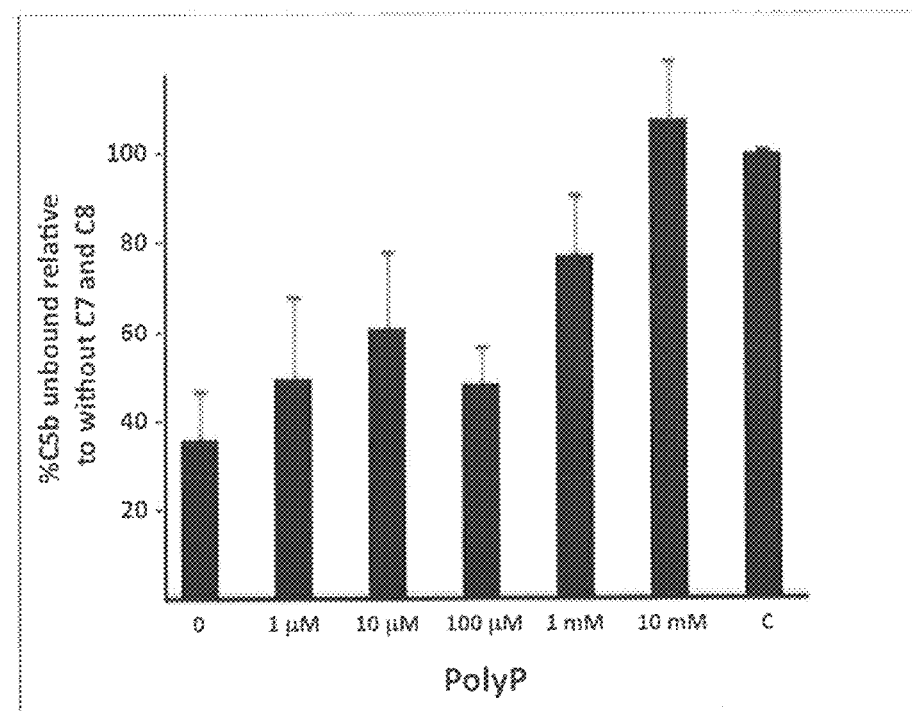
FIGURE 13B FIGURE 17A
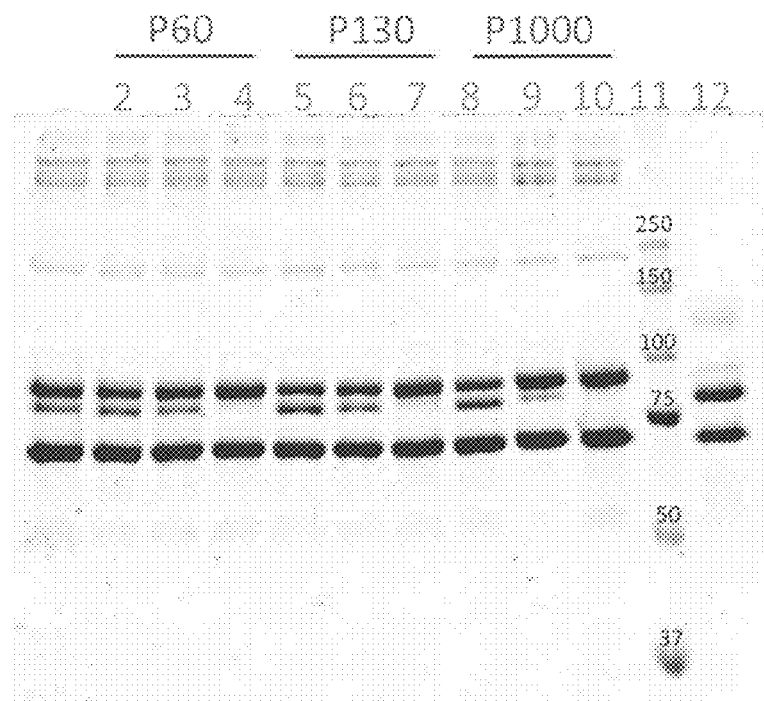
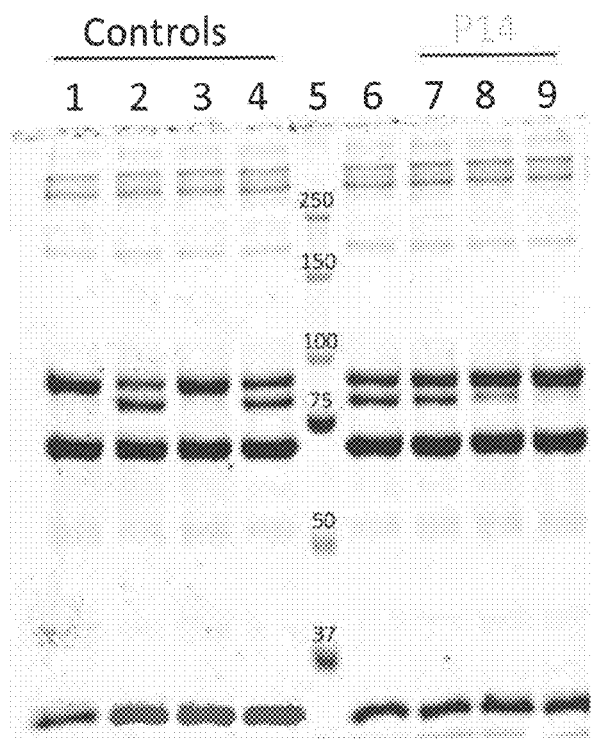
FIGURE 17B PolyP 0 μM + 10% $H_2O_2$ PolyP 500 μM + 10% $H_2O_2$

METHODS FOR INHIBITING COMPLEMENT ACTIVATION AND USES THEREOF

CROSS-REFERENCE TO RELATED APPLICATIONS

This application claims benefit of U.S. Provisional Application No. 61/901,759, filed on Nov. 8, 2013, the disclosure of which is incorporated herein by reference.

FIELD OF THE INVENTION

The present invention provides methods for inhibiting complement activation and uses thereof. More specifically, the present invention provides methods for inhibiting complement activation using polyphosphates.

BACKGROUND OF THE INVENTION

Inorganic polyphosphate (polyphosphate or PolyP) is a linear polymer of orthophosphate, linked by phosphoanhydride bonds[1-3]. It has been found in mammalian cells and lower organisms and localized to lysosomes, dense granules, mitochondria and nuclei. The polyphosphate polymer varies in length from cell to cell and in different organisms, ranging from 60-100 in human platelets, to thousands of phosphate units in some bacteria[4-6]. In platelets, abundant polyphosphate has been localized in dense granules[7] and released upon activation, whereupon it has been found in platelet-rich thrombi at concentrations of 1-3 uM[8]. At physiologic pH, each internal unit has a monovalent negative charge, and thus the polymers are highly anionic. This property led to the finding that polyphosphate can provide a physiologic anionic surface on which factor XII, prekallikrein and high molecular weight kininogen, assemble for contact activation of coagulation[9]. Subsequent studies found that polyphosphate is pro-thrombotic and pro-inflammatory in in vivo mouse models[8,10], acting at multiple steps in the coagulation cascade[8,11-17]. The effects of polyphosphate on coagulation have been found to be concentration- and size-dependent[14]. Thus, platelet-sized polyphosphate ($P_{60-100}$) has been found to primarily accelerate thrombin-mediated activation of factor XI and factor V, while larger size polyphosphate has been found to trigger coagulation via contact activation of factor XII and enhances fibrin polymerization.

The complement system comprises over 30 soluble and membrane-bound proteins, contributing to innate and adaptive immunity, aiding in the disposal of danger-associated molecular patterns. Complement activation, which often occurs in concert with coagulation, is achieved via three pathways—the lectin pathway (LP), the classical pathway (CP) and the alternative pathway (AP). These converge with C3 convertase-mediated transformation of C3 into C3a and C3b. The C3a anaphylatoxin recruits leukocytes and activates platelets[20]. C3b deposition on bacteria promotes opsonization by leukocytes and is required for formation of the C5 convertase that cleaves C5 into C5a and C5b. C5b rapidly binds to C6, forming a tight C5b,6 complex, which then binds to C7, yielding the C5b-7 complex. This attaches to the outer leaflet of a target membrane. The subsequent addition of the heterotrimeric C8αβγ further stabilizes and anchors the now C5b-8 complex to the cell by inducing a conformational change in C8 and burying a hydrophobic tail through the lipid bilayer. Multiple C9 subunits finally join for assembly of the C5b-9 pore-like, lytic membrane attack complex (MAC)[21].

C1-inh is a serine protease inhibitor (serpin) that circulates in the blood and is a major negative regulator of complement activation, interfering with the activation of the lectin and classical pathways by neutralizing MBL-associated serine protease (MASP)1 and C1s, respectively[70,71]. The effect of C1-inh on MASP1 and C1s is augmented by the presence of heparin[72]. PolyP has been shown to bind to C1-inh[69].

Inappropriate complement activation has been implicated in inflammation, immune disorders, and in the pathology of many diseases or disorders.

SUMMARY OF THE INVENTION

The present invention provides, in part, a polyphosphate that specifically binds to a protein or protein complex, or fragment thereof, of the complement system and methods and uses thereof.

In one aspect, the invention provides a method for treating a complement-associated disorder by administering an effective amount of a polyphosphate to a subject in need thereof, where the polyphosphate comprises at least 10 phosphate units. In some embodiments, the method includes ameliorating one or more symptoms associated with the complement-associated disorder.

The complement-associated disorder may be a complement-associated eye disorder, a complement-associated inflammatory disorder, a complement-associated immune disorder, a complement-associated central nervous system disorder, a complement-associated vascular disorder, a complement-associated ischemic disorder, a complement-associated lung disorder, a complement-mediated tissue injury, a complement-associated infection, a complement-associated cancer, an alternative pathway-associated disorder, a lectin pathway-associated disorder, a classical pathway-associated disorder, or a combination of these disorders. In some embodiments, the complement-associated disorder may be age-related macular degeneration, such as dry age-related macular degeneration, or rheumatoid arthritis.

The polyphosphate may be administered using parenteral, intravenous, subcutaneous, intramuscular, intracranial, intraorbital, intravitreal, ophthalmic, intraventricular, intracapsular, intraspinal, intrathecal, intracisternal, intraperitoneal, intranasal, epidermal, sub-epidermal, dermal, sub-dermal, aerosol, systemic, topical, injection, inhalation, lavage, or oral administration techniques. In some embodiments, the polyphosphate may be administered locally to the site of the complement-associated disorder.

The polyphosphate may include between about 10 to about 10,000 phosphate units. In some embodiments, the polyphosphate may be administered to achieve a concentration of about 10 μM to about 10000 μM. In some embodiments, the polyphosphate may be administered in an amount effective to substantially reduce hemolytic activity.

The subject may be a human.

In alternative aspects, the invention provides a method for inhibiting complement activation, by administering an effective amount of a polyphosphate to a subject in need thereof, or by applying a polyphosphate to a surface, where the polyphosphate comprises at least 10 phosphate units. The polyphosphate may inhibit complement activation by one or more of: binding to the C6 complement protein, C1-esterase inhibitor (C1-inh), factor H or factor B; enhancing the activity of C1-inh; interfering with C1s-mediated cleavage of C2; destabilizing the C5b-6 complement protein complex; interfering with C5b,6 interaction with C7; interfering with binding of C5b-7 to a cell membrane; interfering with integration of C5b-7 into a cell membrane; interfering with binding of C5b-8 to a cell membrane; interfering with integration of C5b-8 into a cell membrane; destabilizing the membrane attack complex (MAC); or reducing the amount of C5b-9 deposited on a cell surface.

In some embodiments, the polyphosphate may reduce hemolysis. In some embodiments, the polyphosphate may inhibit complement activation in an ion-independent manner. In some embodiments, the polyphosphate may be applied to the organ prior to transplantation of the organ.

In some embodiments, the surface may be a biomaterial or an organ. In some embodiments, the biomaterial may be exposed to blood or blood products in the body or outside of the body. In some embodiments, the biomaterial may be a medical device, stent vascular graft, heart valve, blood product storage container or bag, or dialysis or filtration device.

In some aspects, the invention provides a method for diagnosing a complement-associated disorder in a subject, by determining the level of complement activation in the presence or absence of a polyphosphate in a sample obtained from the subject, where the polyphosphate comprises at least 10 phosphate units, and where a decrease in the level of complement activation in the presence of the polyphosphate is indicative of a complement-associated disorder. In some embodiments, the method may further include comprising comparing the level of complement activation to a reference or control.

BRIEF DESCRIPTION OF THE DRAWINGS

These and other features of the invention will become more apparent from the following description in which reference is made to the appended drawings, as follows.

FIGS. 5A-C are graphs showing the effect of polyphosphate on terminal pathway hemolytic activity in serum. 5A: (●) represents $P_1$ and (○) represents polyphosphate$_{>1000}$. The dotted lines represent the IC$_{50}$ for polyphosphate. Results are representative of more than 5 experiments, each performed in triplicate. 5B: The control represents lysis in the absence of CIAP and polyphosphate, but with an equivalent concentration of CIAP digestion buffer. "CIAP" represents lysis in the presence of CIAP but absence of polyphosphate. Values were normalized to baseline lysis from the control condition. Each column represents quadruplicate data points. 5C: Values were normalized to baseline lysis from the control condition in which no phosphate was added. n=3 independent experiments, each performed in triplicate.

FIG. 9 is a photograph of a native gel showing the effect of polyphosphate on the mobility of terminal pathway proteins. Results are representative of 4 independent experiments.

FIGS. 10A-B are graphs showing the effect of polyphosphate on C7 (A) and C5b,6 (B).

FIGS. 11A-E are graphs showing the effect of polyphosphate on the thermal stability of the complement proteins. 11A, B: C5b,6 (FIG. 11B is the boxed region of FIG. 11A); 11C: C5; 11D: C6; and 11E: C7. Controls are protein without phosphate.

FIGS. 13A-B are graphs showing the effect of polyphosphate on the binding of C5b-8 (A) and C5b-7 (B) complexes to erythrocyte membranes. The results reflect the averages of 3 independent experiments. Error bars indicate standard deviation.

FIGS. 17A-B are photographs of gels showing the effect of polyphosphate size on C4 cleavage by C1s in the presence of C1-inh. The control is C4+C1s+2.5 nM C1-inh (lanes 1) 17A: Lanes 2-4 are C4+C1s+2.5 nM C1-inh with increasing concentrations of polyP$_{60}$ (10 μM, 50 μM and 250 μM). Lanes 5-7 are C4+C1s+2.5 nM C1-inh with increasing concentrations of polyP$_{130}$ (10 μM, 50 μM and 250 μM). Lanes 8-10 are C4+C1s+2.5 nM C1-inh with increasing concentrations of polyP$_{1000}$ (10 μM, 50 μM and 250 μM). Lane 12 is C4. 17B: Controls are C4 (lane 1), C4+C1s (lane 2), C4+C1s+25 nM C1-inh (lane 3) and C4+C1s+2.5 nM C1-inh (lane 4). Lane 6 is C4+C1s+2.5 nM C1-inh with 500 μM Na$_3$PO$_4$. Lanes 7-9 are C4+C1s+2.5 nM C1-inh with increasing concentrations of polyP$_{14}$ (10 μM, 150 μM and 500 μM).

DETAILED DESCRIPTION

Figure 1:
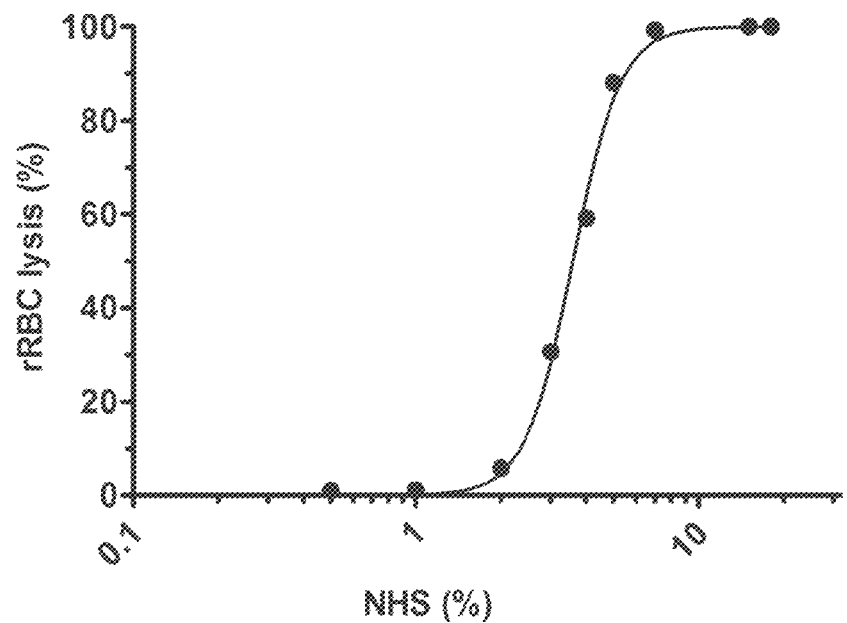
FIG. 1 is a graph showing a standard curve for the total complement-mediated hemolytic assay.

The present disclosure provides, in part, a polyphosphate that specifically binds to a protein or protein complex, or fragment thereof, of the complement system and methods and uses thereof.

Polyphosphates

Polyphosphate, or high-polymeric inorganic polyphosphate, polyphosphate polymer or "polyP," as used herein, refers to a polymer of orthophosphates (Pi) linked by phosphoanhydride bonds. The polyphosphate may be linear. The polyphosphate may be a single chemical entity or it may be a mixture of polyphosphates with different numbers of phosphate units.

In some embodiments, a polyphosphate may be referred to as "polyP$_n$," where "n" refers to the number of phosphate units or the average number of phosphate units. In some embodiments, the number of phosphate units or the average number of phosphate units may be about 4 to about 10,000, or any number in between. In some embodiments, the number of phosphate units or the average number of phosphate units may be about 10 to about 5000 phosphate units, or any number in between. In some embodiments, the number of phosphate units or the average number of phosphate units may be about 20 to about 1500 phosphate units, or any number in between. For example, in some embodiments, the number of phosphate units or the average number of phosphate units may be about 4, 5, 6, 7, 8, 9, 10, 15, 20, 25, 50, 75, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2500, 3000, 3500, 4000, 4500, 5000, 5500, 6000, 6500, 7000, 7500, 8000, 8500, 9000, 9500 or 10000.

In some embodiments, the polyphosphate units may range in size plus or minus about 20% from the average, or any value less that about plus or minus about 20%, such as plus or minus about 15%, 10% or 5%. In some embodiments, over 80% (such as 85%, 90%, 95%, or 99%) of the polyphosphate units may be the size indicated as the average. In general, the polyphosphate may be of any size, as long as the polyphosphate is capable of inhibiting complement activation or binding a protein or fragment thereof, or a protein complex, of the complement system, such as C6, C5b,6, C5b-9, or C1-inh. In some embodiments, a polyphosphate including at least about 4 phosphate units, for example, 4, 5, 10, 14, 15, 30, 60, or more, may be useful as a C1-inh inhibitor. In some embodiments, a polyphosphate including about 30 to about 10,000 phosphate units, or any number in between, may be useful in interfering with the terminal pathway.

In some embodiments, the polyphosphates are provided at a concentration of at least 5 μM or more. In some embodiments, the polyphosphates are provided at a concentration of about 5 μM to about 10,000 μM, or any number in between, such as 5, 6, 7, 8, 9, 10, 15, 20, 25, 50, 75, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2500, 3000, 3500, 4000, 4500, 5000, 5500, 6000, 6500, 7000, 7500, 8000, 8500, 9000, 9500 or 10000 μM.

In some embodiments, the polyphosphate can be complexed with metals, such as alkali earth metals, alkaline earth metals or transition metals, such as $Fe^{3+}$, $Fe^{2+}$, $Pb^{2+}$, $Co^{2+}$, $Cu^{2+}$, $Ni^{2+}$, $Zn^{2+}$, $Mn^{2+}$, $Mg^{2+}$, $Ca^{2+}$, $Sr^{2+}$, $Ba^{2+}$ or $Ag^{2+}$.

A polyphosphate, as described herein, may be purified from natural sources or may be chemically synthesized. In some embodiments, the polyphosphate can be "substantially pure," e.g., when it is separated from the components that naturally accompany it. Typically, a compound is substantially pure when it is at least 10%, 20%, 30%, 40%, 50%, or 60%, more generally 70%, 75%, 80%, or 85%, or over 90%, 95%, or 99% by weight, of the total material in a sample. Thus, for example, a polyphosphate that is chemically synthesized or isolated by known purification techniques will be generally be substantially free from its naturally associated components. A substantially pure polyphosphate can be obtained, for example, by extraction from a natural source or by chemical synthesis. Purity can be measured using any appropriate method such as column chromatography, gel electrophoresis, HPLC, etc. In some embodiments, polyphosphates may be isolated from organisms, such as bacteria or yeast. In alternative embodiments, polyphosphates may be produced by dehydration at high temperatures or by enzymatic synthesis. In alternative embodiments, polyphosphates may be chemically synthesized. Techniques for preparing polyphosphates are well known in the art.

In some embodiments, the polyphosphate can be bound to another compound, such as a polymer, or to a substrate. In some embodiments, the polyphosphate may form a conjugate that affects the polyphosphate's pharmacological properties, such as its pharmacokinetic parameters. The term "conjugate" applies to any composition that comprises at least two moieties, which are attached directly or through a linking group, ligand, or carrier molecule. Suitable compounds are known in the art, and may include without limitation poly (ethylene) glycol (PEG), albumin, dextran and/or polysialic acids (PSAs). In some embodiments, the polyphosphate is conjugated to a polymer which prolongs the polyphosphate's biological half-life in vivo. Biological half-life is a time point at which half of the administered amount of the polyphosphate or conjugate thereof remains in the serum or plasma. The chain length of the polyphosphate may also be altered to affect the polyphosphate's biological half-life. For example, increasing the length of the polyphosphate may prolong its biological half-life. In some embodiments, the polyphosphate's biological half-life is altered according to the complement-associated disease or disorder being treated.

In some embodiments, the polyphosphate can be isolated or unbound or i.e., not chemically attached to any other compound or substrate. In some embodiments, the polyphosphate can be in a soluble form.

The Complement System

The complement system comprises over 30 soluble and membrane-bound proteins ("complement proteins") that contribute to innate and adaptive immunity by acting in a coordinated cascade. Complement activation is achieved via three pathways—the lectin pathway (LP), the classical pathway (CP) and the alternative pathway (AP). The three pathways converge with C3 convertase-mediated transformation of C3 into C3a and C3b, which form the C5 convertase that cleaves C5 into C5a and 5b. C5b rapidly binds to C6, forming a tight C5b,6 complex, which then binds to C7, yielding the C5b-7 complex which attaches to the outer leaflet of a target membrane. The subsequent addition of the heterotrimeric C8αβγ further stabilizes and anchors the now C5b-8 complex to the cell by inducing a conformational change in C8 and burying a hydrophobic tail through the lipid bilayer. Multiple C9 subunits finally join for assembly of the C5b-9 pore-like, lytic membrane attack complex (MAC). Complement activation therefore refers to any step in the complement cascade. C1-inh is a serine protease inhibitor (serpin) that circulates in the blood and is a major negative regulator of complement activation, interfering with the activation of the lectin and classical pathways.

As used herein, complement proteins or components include without limitation the C1, C1-inh, C5, C6, C7, C8, or C9 proteins, factor B, factor H, factor I, properdin, C2, C3, C4, C1q, C1r, C1s, Mannose binding lectin (MBL) and the associated serine proteases (MASPs), clusterin, vitronectin, CD46, CD55, CD59, thrombomodulin, as well as biologically-active fragments thereof, as well as any protein complexes that include complement proteins or fragments thereof, such as C5b,6 or C5b-9.

Complement-Associated Disorders

Complement-associates disorders include, without limitation, disorders associated with inappropriate, aberrant or excessive complement activation. In some embodiments, a complement-associated disorder may, for example, result from an insult or injury potentially leading to tissue damage and/or cytotoxic responses. Accordingly, the terms "disease" or "disorder" refer to any condition, illness, insult, injury, harm, pathological condition, or other term of art that implies a harmful or detrimental physiological condition resulting from inappropriate, aberrant or excessive complement activation. In some embodiments, a complement-associated disorder does not include a coagulation disorder, such as a disorder associated with inappropriate or aberrant coagulation.

In some embodiments, a complement-associated disorder includes any disorder associated with or mediated by a complement protein, such as one or more of the C6 complement protein, C1-esterase inhibitor (C1-inh), factor H or factor B. In some embodiments, a complement-associated disorder includes any disorder which would be benefited by one or more of enhancing the activity of C1-inh; interfering with C1s-mediated cleavage of C2; destabilizing the C5b-6 complement protein complex; interfering with C5b,6 interaction with C7; interfering with binding of C5b-7 to a cell membrane; interfering with integration of C5b-7 into a cell membrane; interfering with binding of C5b-8 to a cell membrane; interfering with integration of C5b-8 into a cell membrane; destabilizing the membrane attack complex (MAC); or reducing the amount of C5b-9 deposited on a cell surface. In some embodiments, a complement-associated disorder does not include a disorder associated with or mediated by a coagulation protein.

In some embodiments, a complement-associated disorder includes any disorder associated with increased deposition of C3 or C4 fragments, and/or C5b-9 on the surface of cells, such as vascular cells, endothelial cells, epithelial cells, immune cells, malignant cells, infectious or pathogenic microorganisms, etc. In some embodiments, complement-associated disorders include any disorder associated with increased deposition of C5b-9 on the surface of a cell, such as a vascular endothelial cell or a retinal pigmented epithelial cell.

In some embodiments, complement-associated disorders include without limitation an alternative pathway-associated disorder, a lectin pathway-associated disorder, a classical pathway-associated disorder, or a combination thereof.

In some embodiments, complement-associated disorders include without limitation complement-associated immune-related disorders, including complement-associated autoimmune disorders; complement-associated inflammatory disorders; complement-associated central nervous system disorders; complement-associated vascular disorders; complement-associated ischemic disorders; complement-associated lung disorders; complement-associated eye disorders; complement-mediated tissue injuries; complement-associated infections; complement-associated cancers etc.

In some embodiments, complement-associated disorders include without limitation disorders such as complement-associated arthritis, such as rheumatoid arthritis (RA), recalcitrant rheumatoid arthritis, type II collagen-induced arthritis, post-traumatic and degenerative arthritis, juvenile chronic arthritis, etc.; spondyloarthropathies; complement-associated renal disease such as chronic kidney disease, glomerulonephritis, dense deposit disease (DDD), tubulointerstitial nephritis, lupus nephritis, type II membranoproliferative glomerulonephritis, IgA nephropathy, acute renal failure, and Henoch-Schönlein purpura nephritis; systemic lupus erythamatosus; complement-associated transplantation disorders, including graft-versus host disease, allo-transplantation, and graft rejection such as xenotransplant rejection, hyperacute allograft and hyperacute xenograft rejection; Crohn's disease; complement-associated vasculitis including immune-complex-induced vasculitis, Pauci-immune vasculitis, systemic lupus erythematosus-associated vasculitis, immune complex vasculitis, systemic vaculitis; myasthenia gravis; inflammatory bowel disease (IBD); systemic sclerosis (scleroderma); idiopathic inflammatory myopathies such as dermatomyositis and polymyositis; Sjogren's syndrome; complement-associated anemias such as hemolytic anemia, autoimmune hemolytic anemia (AIHA), immune pancytopenia, and paroxysmal nocturnal hemoglobinuria; complement-associated thrombocytopenias such as autoimmune thrombocytopenia, idiopathic thrombocytopenic purpura (ITP), immune-mediated thrombocytopenia; thromboembolism; hemolysis, elevated liver enzymes, and low platelets (HELLP) syndrome; thrombotic thrombocytopenic purpura (TTP); atypical hemolytic uremic syndrome, typical or infectious hemolytic uremic syndrome; hemodialysis; cryoglobulemia; hereditary angioedema; complement-associated thyroiditis such as Graves' disease, Hashimoto's thyroiditis, juvenile lymphocytic thyroiditis, and atrophic thyroiditis; demyelinating diseases of the central and peripheral nervous systems such as multiple sclerosis; Alzheimer's disease; Parkinson's disease; traumatic brain injury; neurodegenerative conditions; neuropathic pain; idiopathic polyneuropathy; neuromyelitis optica (NMO); multifocal motor neuropathy (MMN); experimental allergic neuritis; hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis; inflammatory and fibrotic lung diseases such as cystic fibrosis, allergic diseases of the lung such as eosinophilic pneumonia, idiopathic pulmonary fibrosis and hypersensitivity pneumonitis; sarcoidosis; autoimmune or immune-mediated skin diseases such as bullous skin diseases, erythema multiforme, contact dermatitis, and psoriasis; complement associated eye disorders including without limitatation macular degeneration, such as age-related macular degeneration (AMD) including dry age-related macular degeneration; choroidal neovascularization (CNV); corneal neovascularization; retinal neovascularization; Central Retinal Vein Occlusion (CRVO); uveitis; von Hippel-Lindau disease; pathological myopia; histoplasmosis of the eye; endophthalmitis; retinopathies, including diabetic retinopathies or other ischemia-related retinopathies; diabetic macular edema; complement-associated vascular disorders, such as cardiovascular disorder, myocarditis, a cerebrovascular disorder, a peripheral (e.g., musculoskeletal) vascular disorder, a renovascular disorder, a mesenteric/enteric vascular disorder; complement-associated ischemic disorders such as myocardial infarction, stroke, renal ischemia/reperfusion, injury due to cardiopulmonary bypass surgery; ischemia-reperfusion injury; dilated cardiomyopathy; cardiogenic shock; cardioplegia-induced coronary endothelial dysfunction; autoimmune heart disease; dermatomyositis; urticaria such as chronic idiopathic urticaria; gluten-sensitive enteropathy, Whipple's disease, adult respiratory distress syndrome (ARDS); chronic occlusive pulmonary distress syndrome (COPD); asthma; aspiration pneumonia; thermal injury such as burn and frostbite; extracorporeal dialysis and blood oxygenation; colitis, peritonitis, sepsis, systemic inflammatory syndrome, septic shock, periodontitis; obesity; metabolic syndrome; spontaneous fetal loss, epidermolysis bullosa, recurrent fetal loss; endometriosis; Takayasu's disease, diabetes mellitus; type I diabetes; diabetic angiopathy; Kawasaki's disease (arteritis); venous gas embolus (VGE); restenosis following stent placement; rotational atherectomy; angioplasty; percutaneous transluminal coronary angioplasty (PTCA); coronary artery disease (CAD); dermatomyositis; atherosclerosis; spinal cord injury, pemphigus; Goodpasture syndrome; Degos disease; antiphospholipid syndrome (APS); catastrophic APS (CAPS); Barraquer-Simons Syndrome; recurrent infections; etc.

In some embodiments, complement-associated cancers include without limitation lymphomas (Hodgkins and non-Hodgkins), B cell lymphoma, T cell lymphoma, myeloid leukemia, leukemias, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumours, myelomas, AJDS-related lymphomas or sarcomas, metastatic cancers, bladder cancer, brain cancer, nervous system cancer, squamous cell carcinoma of head and neck, neuroblastoma glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colo-rectal cancers, prostatic cancer, or pancreatic cancer.

In some embodiments, complement-associated infections include without limitation viral infections, bacterial infections, parasitic infections and fungal infections. The viral infections may be due to Herpes simplex viras type-1, Herpes simplex viras type-2, Cytomegaloviras, Epstein-Ban virus, Naricella-zoster viras, Human herpesvirus 6, Human herpesvirus 7, Human herpesvirus 8, Variola virus, Vesicular stomatitis viras, Hepatitis A viras, Hepatitis B virus, Hepatitis C viras, Hepatitis D viras, Hepatitis E viras, Rhinoviras, Coronavirus, Influenza viras A, Influenza viras B, Measles viras, Polyomaviras, Human Papilomaviras, Respiratory syncytial virus, Adenovirus, Coxsackie viras, Dengue viras, Mumps viras, Polioviras, Rabies viras, Rous sarcoma viras, Yellow fever viras, Ebola viras, Marburg virus, Lassa fever virus, Eastern Equine Encephalitis viras, Japanese Encephalitis viras, St. Louis Encephalitis virus, Murray Valley fever viras, West Nile viras, Rift Valley fever viras, Rotavirus A, Rotavirus B, Rotavirus C, Sindbis viras, Simian Immunodeficiency ciras, Human T-cell Leukemia virus type-1, Hantavirus, Rubella viras, Simian Immunodeficiency virus, Human lmmx odeficiency viras type-1, and Human Immunodeficiency virus type-2.

The bacterial infection may be due to *Mycobacterium tuberculosis, Mycobacterium bovis, Mycobacterium avium, Mycobacterium intracellulare, Mycobacterium africanum, Mycobacterium kansasii, Mycobacterium marinum, Nocardia* species, *Legionella* species, *Salmonella* species, *Shigella* species, *Yersinia* pestis, *Pasteurella* species including *Pasteurella haemolytica* and *Pasteurella multocida, Actinobacillus pleuropneumoniae, Listeria monocytogenes, Listeria ivanovii, Brucella* species, *Cowdria ruminantium, Chlamydia pneumoniae, Chlamydia trachomatis, Chlamydia psittaci, Coxiella burnetti, Rickettsial* species, *Ehrlichia* species, *Staphylococcus aureus, Staphylococcus epidermidis, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa, Hemophilus* species including *Haemophilus influenzae* and *Haemophilus influenzae, Clostridium* species, *Yersinia* species.

The parasitic infection may be due to *Toxoplasma gondii, Plasmodium* species including *Plasmodium falciparum, Plasmodium vivax, Plasmodium malariae, Trypanosoma brucei, Trypanosoma cruzi, Leishmania* species, *Schistosoma* species, *Entamoeba histolytica.*

The fungal infection may be due to *Candida albicans, Cryptococcus neoformans, Histoplasma capsulatum,*

*Aspergillus fumigatus, Coccidiodes immitis, Paracoccidiodes brasiliensis, Blastomyces dermitidis, Pneomocystis carnii, Penicillium marneffi, Alternaria alternata.*

Therapeutic or Diagnostic Uses, Compositions, Dosages and Administration

Polyphosphates, as described herein, can be used for a variety of diagnostic, therapeutic or other purposes.

In some embodiments, polyphosphates can be used to treat a variety of complement-associated disorders, as described herein. In general, the polyphosphates can be used in the treatment or prophylaxis of, or to ameliorate one or more symptoms associated with, any disease, disorder or condition, which would be benefited by inhibiting complement activation. In some embodiments, inhibition of complement activation may be by one or more of: binding to the C6 complement protein, C1-esterase inhibitor (C1-inh), factor H or factor B; enhancing the activity of C1-inh; interfering with C1s-mediated cleavage of C2; destabilizing the C5b,6 complement protein complex; interfering with C5b,6 interaction with C7; interfering with binding of C5b-7 to a cell membrane; interfering with integration of C5b-7 into a cell membrane; interfering with binding of C5b-8 to a cell membrane; interfering with integration of C5b-8 into a cell membrane; destabilizing the membrane attack complex (MAC); or reducing the amount of C5b-9 deposited on a cell surface. In some embodiments, inhibition of complement activation includes negative regulation of complement activation. In some embodiments, the polyphosphate inhibits complement activation in an ion-independent manner. In some embodiments, the polyphosphate inhibits complement activation by reducing hemolysis.

By "inhibiting complement activation" is meant reducing or decreasing the level of activity of a complement pathway, or by interfering with an aspect of a complement pathway. In some embodiments, by "inhibiting complement activation" is meant reducing or decreasing the formation of a particular complement complex such as C5b,6; C5b-7; C5b-8 or C5b-9. In some embodiments, by "inhibiting complement activation" is meant reducing or decreasing the amount of C5b-9 deposited on a cell surface. In some embodiments, by "inhibiting complement activation" is meant reducing or decreasing the binding or integration of C5b-7 or C5b-8 into a cell membrane. The reduction or decrease may be a change of any value between about 10% and about 90%, e.g., 10%, 20%, 30%, 40%, 50%,60%, 70%, 80%, 90%, or may be over 100%, when compared with a control or reference.

Inhibition of complement activation can be measured by methods well known in the art such as, for example, by a conventional hemolytic assay such as the hemolysis assay described by Kabat and Mayer (eds), "Experimental Immunochemistry, $2^{nd}$ Edition," 135-240, Springfield, Ill., C C Thomas (1961), pages 135-139, or as described herein.

In some embodiments, a pharmaceutical composition according to the present disclosure can include a polyphosphate and a pharmaceutically acceptable carrier. Such compositions can be suitable for use in treatment of complement-associates disorders as described herein. In some embodiments, a polyphosphate can be administered alone or in combination with other compounds (for example, nucleic acid molecules, small molecules, peptides, or peptide analogues), in the presence of a liposome, an adjuvant, or any pharmaceutically acceptable carrier, in a form suitable for administration to mammals, for example, humans, cattle, sheep, etc. If desired, treatment with a polyphosphate may be combined with more traditional and existing therapies for a complement-associated disorder or for inhibiting complement activation.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt.

The pharmaceutical composition can be formulated in a variety of forms including, without limitation, liquid, semi-solid and solid dosage forms, such as liquid solutions (e.g., injectable and infusible solutions), dispersions or suspensions, tablets, pills, powders, liposomes and suppositories. The appropriate form depends, in part, on the intended mode of administration and therapeutic application. In some embodiments, the pharmaceutical composition can be formulated as a solution, microemulsion, dispersion, liposome, or other ordered structure suitable for stable storage.

The pharmaceutical composition may be formulated according to standard methods. Pharmaceutical formulation is a well-established art, and is further described in, e.g., Gennaro (2000) "Remington: The Science and Practice of Pharmacy," $20^{th}$ Edition, Lippincott, & Wilkins (ISBN: 0683306472). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

In certain embodiments, the polyphosphate may be prepared with a carrier that will protect the polyphosphate against rapid release, such as a controlled release formulation, including implants and microencapsulated delivery systems, Biodegradable, biocompatible polymers can be used, such as ethylene vinyl acetate, polyanhydrides, polyglycolic add, collagen, polyorthoesters, and polylactic acid.

In some embodiments, a polyphosphate can be modified, e.g., with a moiety that improves its stabilization and/or retention in circulation, e.g., in blood, serum, or other tissues.

A pharmaceutical composition can include a effective amount of polyphosphate as described herein. Such effective amounts can be readily determined by one of ordinary skill in the art based, in part, on the effect of the administered polyphosphate, or the combinatorial effect of polyphosphate and one or more additional active agents, if more than one agent is used.

In some embodiments, polyphosphates are administered to a subject in an amount sufficient to inhibit complement activation. The pharmaceutical composition can be administered to a subject, e.g., a human subject, using a variety of methods that depend, in part, on the route of administration. Any appropriate route of administration may be employed, for example, parenteral, intravenous, subcutaneous, intramuscular, intracranial, intraorbital, intravitreal, ophthalmic, intraventricular, intracapsular, intraspinal, intrathecal, intracisternal, intraperitoneal, intranasal, epidermal, sub-epidermal, dermal, sub-dermal, aerosol, systemic, topical, injection, inhalation, lavage, or oral administration. Therapeutic formulations may be in the form of liquid solutions or suspensions;

for oral administration, formulations may be in the form of tablets or capsules; and for intranasal formulations, in the form of powders, nasal drops, or aerosols. In some embodiments, the route can be, e.g., intravenous injection or infusion (IV), subcutaneous injection (SC), intraperitoneal (IP), intrapulmonary, intraocular, intravitreal, or intramuscular injection. Certain inhibitors, e.g., small molecules, can be orally administered to a subject.

A "subject," as used herein, may be any mammal. For example, a subject may be without limitation a human (e.g., a patient), a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant). In some embodiments, the subject may be a female or may be a male. The subject may be a clinical patient, a clinical trial volunteer, an experimental animal, etc. The subject may be suspected of having or at risk for having a complement associated disorder, be diagnosed with a complement associated disorder, or be a control subject that is confirmed to not have a complement associated disorder. In some embodiments, the subject may be confirmed to not have a coagulation disorder. Diagnostic methods for complement associated disorders and the clinical delineation of such diagnoses are known to those of ordinary skill in the art. As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition including a polyphosphate). In some embodiments, the methods can include identifying the subject as one having, suspected of having, or at risk for developing, a complement-associated disorder.

An "effective amount" of a pharmaceutical composition according to the invention includes a therapeutically effective amount or a prophylactically effective amount. A "therapeutically effective amount" refers to an amount of polyphosphate effective, at dosages and for periods of time necessary, to achieve the desired therapeutic result, such as treatment of a complement-associated disorder. A therapeutically effective amount of a polyphosphate may vary according to factors such as the disease state, age, sex, and weight of the subject, and the ability of the polyphosphate to elicit a desired response in the subject. Dosage regimens may be adjusted to provide the optimum therapeutic response. A therapeutically effective amount is also one in which any toxic or detrimental effects of the polyphosphate are outweighed by the therapeutically beneficial effects. Determination of a therapeutically effective dose of a polyphosphate is well within the capability of those skilled in the art. For example, the therapeutically effective dose can be estimated initially either in cell culture assays, or in animal models, such as those described herein. A "prophylactically effective amount" refers to an amount of polyphosphate effective, at dosages and for periods of time necessary, that achieves the desired prophylactic result, such as delay in onset of symptoms of a complement-associated disorder. Animal models can also be used to determine the appropriate concentration range and route of administration. Such information can then be used to determine useful doses and routes for administration in other animals, including humans, using standard methods known to those of ordinary skill in the art. A preferred range for therapeutically or prophylactically effective amounts of a polyphosphate may be any integer from 0.1 nM-0.1M, 0.1 nM-0.05M, 0.05 nM-15 µM or 0.01 nM-10 µM. In general, the lowest effective dosage may be used. In some embodiments, the dosage may be lower than plasma concentrations. In some embodiments, the dosage may be a dosage that is not suitable for treatment or prophylaxis of a coagulation or other disorder.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active polyphosphate in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

The skilled person will therefore recognize that the dosage to be administered is not subject to defined limits. Prior to administration for therapeutic purposes, the dosage of the polyphosphate may need to be modified or adapted for the particular purpose, for example the concentration of polyphosphate needed for whole body administration may differ from that used for local administration. Similarly, the toxicity of the polyphosphate may change depending upon the mode of administration and overall composition being used (e.g., buffer, diluent, additional chemotherapeutic, etc.).

Polyphosphate compositions according to the invention may be provided chronically or intermittently. "Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

In some embodiments, a subject chronically treated with a polyphosphate can be treated for a period of greater than or equal to 2 weeks (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks; 1, 2, 3, 4, 5, 6, 7, 8, 9, 10, 11, or 12 months; or 1, 1.5, 2, 2.5, 3, 3.5, 4, 4.5, 5, 5.5, 6, 6.5, 7, 7.5, 8, 8.5, 9, 9.5, 10, 10.5, or 12 years or for the remainder of the subject's life) with the polyphosphate in an amount and with a dosing frequency that are sufficient to maintain a concentration of the polyphosphate in the subject that inhibits or substantially inhibits complement activation.

In some embodiments, polyphosphates can be used to detect, diagnose or prognose a variety of complement-associated disorders, as described herein. In general, the polyphosphates can be used in the diagnosis, prognosis or detection of any disease, disorder or condition, in which complement activation plays a role. Accordingly, in some embodiments, polyphosphates may be used to measure disease-associated changes in complement activation, or to assess the function of a complement protein, complex and/or pathway that is regulated or mediated by polyphosphate.

In some embodiments, a sample obtained from a subject may be assayed for complement activation in the presence or absence of a polyphosphate, where a decrease in complement activation in the presence of the polyphosphate is indicative of a complement-associated disorder. In some embodiments, a reference or control may be used.

In some embodiments, complement activation mediated by a polyphosphate may be determined by one or more of: binding to the C6 complement protein, C1-esterase inhibitor (C1-inh), factor H or factor B; enhancing the activity of C1-inh; interfering with C1s-mediated cleavage of C2; destabilizing the C5b,6 complement protein complex; interfering with C5b,6 interaction with C7; interfering with binding of C5b-7 to a cell membrane; interfering with integration of C5b-7 into a cell membrane; interfering with binding of C5b-8 to a cell membrane; interfering with integration of C5b-8 into a cell membrane; destabilizing the membrane attack complex (MAC); or reducing the amount of C5b-9 deposited on a cell surface.

In some embodiments, diagnosis of a complement-associated disorder may be performed by determining reduction of hemolysis mediated by a polyphosphate.

Suitable assays are known in the art or described herein.

Other Uses

In some embodiments, polyphosphates can be applied to a surface, such as a biomaterial or an organ. In some embodiments, polyphosphates can be used to suppress the deposition of complement activation products on the surface.

In some embodiments, the polyphosphates can be used to protect biomaterials exposed to blood or blood products in the body or outside of the body. The biomaterial can be a medical device, such as a stent; vascular grafts, heart valves, blood product storages containers and bags, dialysis and filtration devices, etc.

The polyphosphates may be selectively modified (e.g., adding an amine group to the end of the polyphosphates) to adjust the binding preferences of the polyphosphates to a biomaterial surface. Determination of an appropriate modification of the polyphosphates, as well as techniques that enable selectively modifying polyphosphates, is well within the capability of those skilled in the art.

The organ can be any organ capable of being transplanted, such as heart, lung, kidney, etc. In some embodiments, the polyphosphate can be applied to the organ prior to transplantation of the organ.

In some embodiments, the polyphosphates are provided at a concentration of at least 5 µM or more. In some embodiments, the polyphosphates are provided at a concentration of about 5 µM to about 10,000 µM, or any number in between, such as 5, 6, 7, 8, 9, 10, 15, 20, 25, 50, 75, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2500, 3000, 3500, 4000, 4500, 5000, 5500, 6000, 6500, 7000, 7500, 8000, 8500, 9000, 9500 or 10000 µM.

The present invention will be further illustrated in the following examples.

EXAMPLES

Example 1

Materials and Methods

Reagents.

Chemicals were purchased from Sigma-Aldrich (St. Louis, Mo., USA) unless otherwise stated. Polyphosphate preparations were synthesized, size-fractionated and quantified by the malachite green assay as described[14], with concentrations expressed in terms of phosphate monomers (monomer formula: $NaPO_3$). Mean number or range of phosphate units comprising polyphosphate are indicated in the subscript. Gelatin veronal buffer (GVB, pH7.4), normal human serum (NHS), and human plasma-derived C5b,6, C7, C8, and C9 were from Complement Technology, Inc. (Tyler, Tex., USA). Rabbit erythrocytes (rRBC) were freshly obtained from citrated venous blood following venipuncture performed by Animal Care Services technicians at the University of British Columbia, with approval by the local Animal Ethics committee. Chicken erythrocytes (cRBC) were from Colorado Serum Company (Denver, Colo., USA). Hemolytic assays were performed in 96-well non-treated microplates from Corning (Amsterdam, Netherlands). SYPRO Orange was from Invitrogen (Burlington, ON, Canada).

Hemolytic Assays.

Erythrocyte lysis assays were used to measure complement-mediated hemolytic activity. Erythrocyte (RBC) lysis assays as previously described[18,37] were used to measure complement activity. For alternative pathway assays and for total hemolytic activity assays, unsensitized rabbit erythrocytes were used. Chicken erythrocytes were used for the terminal pathway assays.

Erythrocytes were washed three times in GVB with the reaction buffers as indicated, and counted using the Advia 120 Hematology System from Siemens (Siemens, Erlangen, Germany). Reactions in 300 µL were allowed to proceed for 30 min at 37° C., after which unlysed cells were pelleted by centrifugation at 600×g. Erythrocyte lysis, reflected by the released hemoglobin in the supernatant, was quantified by measuring the absorbance at 405 nm using the Mithras LB 940 microplate reader from Berthold Technologies (Bad Wildbad, Germany). Percent lysis was determined relative to the control of 100% lysis with $H_2O$. For total hemolytic and terminal pathway (TP) assays, the concentrations of NHS and C5b,6 to initiate complement activation were established from pilot studies to obtain ~70-80% erythrocyte lysis at 30 min.

For total hemolytic activity assays, normal human serum (NHS) (4.5%), polyphosphate, and rabbit erythrocytes (rRBC) ($6.0 \times 10^7$ cells/mL) were added sequentially to initiate lysis. Reagents were diluted in GVB. Reactions were stopped by the addition of 30 mM EDTA in GVB. Lysis in the absence of NHS was subtracted as background. A standard curve for the total complement-mediated hemolytic assay (FIG. 1) was generated by incubating increasing concentrations of normal human serum with rabbit erythrocytes for 30 min at 37° C., quenching the reaction with excess EDTA, and then measuring the $A_{405}$ of the supernatant. Increasing absorbance corresponds to increasing hemoglobin release from lysed red blood cells. The linear region of the curve was determined to be between 20-80% lysis, corresponding to 2.5-4.5% serum. Since the effects of polyphosphate were determined in pilot studies to be inhibitory, baseline lysis was fixed at ~80% (using 4.5% serum). The effects of polyphosphate over a range of concentrations under these experimental conditions was subsequently evaluated.

Figure 2:
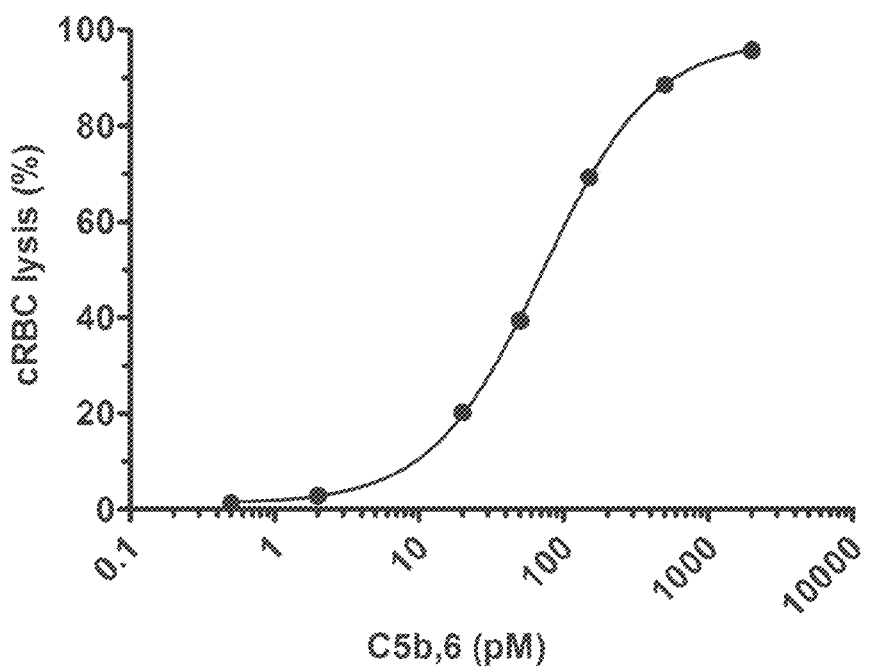
FIG. 2 is a graph showing a standard curve for the terminal pathway assay using serum as the source of complement.

For serum-based terminal pathway (TP) hemolytic assays, components were diluted in GVB containing 10 mM EDTA (GVB-E), the latter added to prevent upstream complement activation and generation of endogenous C5b,6. 2% NHS was used as the source of C7, C8, and C9, and hemolysis of chicken erythrocytes (cRBC) ($3.3 \times 10^8$ cells/mL) was initiated by addition of exogenous purified C5b,6, the concentration of which was determined from pilot studies to yield ~70-80% lysis at 30 min. No C5b,6 activity was detected in the NHS prior to initiating the reaction. For some experiments, instead of NHS, purified terminal pathway complement components were used in the TP assays. In these assays, in a final volume of 300 uL GVB, lysis was achieved by the sequential addition of the following components: cRBC (3.3× $10^8$ cells/mL), C5b,6 (20 µM), C7 (15 nM), C8 (10 nM), and C9 (25 nM). The unlysed cell pellet was removed by centrifugation and lysis was measured immediately after the 30-minute reaction. A standard curve for the terminal pathway assay using serum as the source of complement (FIG. 2) was generated using a fixed serum concentration at 2%, and increasing concentrations of purified C5b,6 dose-dependently lysed chicken erythrocytes after 30 min at 37° C. The linear region of the curve was achieved with 20-250 µM purified C5b,6. 250 µM of purified C5b,6 was therefore used to fix baseline lysis at ~80% to allow assessment of the inhibitory effects of polyphosphate in serum.

Figure 3:
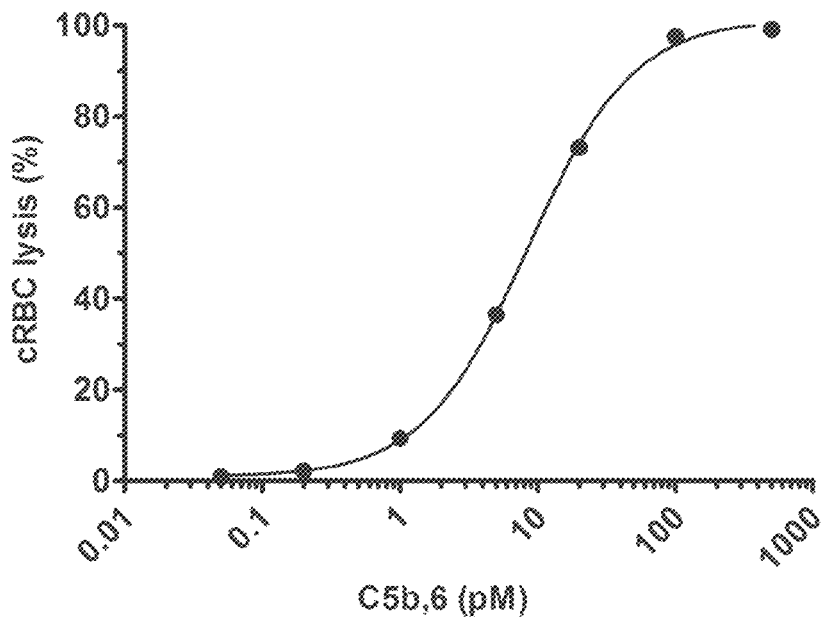
FIG. 3 is a graph showing a standard curve for the terminal pathway assay using purified complement components.

A standard curve for the terminal pathway assay using purified complement components (FIG. 3) was generated using C7 (15 nM), C8 (10 nM), and C9 (25 nM) in excess, and hemolysis of chicken erythrocytes after 30 min at 37° C. was determined as dependent on the concentration of purified C5b,6. The linear region of the curve was achieved with 2-20 pM purified C5b,6. 20 pM of purified C5b,6 was therefore used to fix baseline lysis at ~80% and this was used to assess the inhibitory effects of polyphosphate.

Results were normalized to this amount of lysis, and shown in figures as "relative RBC lysis". All results are representative of experiments performed in triplicate, a minimum of 3 times.

Calf Intestinal Alkaline Phosphatase (CIAP) Digestion of Polyphosphate (polyP).

600 µM polyP was incubated with 400 U/mL calf intestinal alkaline phosphatase (CIAP; Invitrogen Life Technologies Inc., Burlington, ON, Canada) for 18 hrs in TBS (20 mM Tris-HCl, 150 mM NaCl, pH 8.4) in the presence of 2 mM $MgCl_2$ and 0.2 mM $ZnCl_2$. Complete digestion of polyP into monomers was confirmed by TBE-urea polyacrylamide gel electrophoresis followed by staining with 0.05% toluidine blue and by the malachite green assay[68]. CIAP-treated polyP was added to the TP assay at a final concentration of 100 µM.

Visualization of PolyP in TBE-Urea Gels.

PolyP can be visualized in both native and TBE-urea gels using the metachromatic stain toluidine blue which, upon binding to polyP, shifts the absorption peak from 630 nm to 530 nm. 10 nmol of phosphate were mixed with 5× sample buffer (15% Ficoll 400, 0.25% xylene cyanol FF, 0.25% bromophenol blue, 5×TBE) and loaded into 10% TBE-urea Precast Ready Gels (8.6×6.8) from Bio-Rad. Running buffer was 1×TBE containing 90 mM Tris, 90 mM borate, 2.7 mM EDTA, pH 8.3. Samples were electrophoresed under constant voltage for 30 min at 150 V. Gels were stained with a fixative solution containing toluidine blue (0.05% toluidine blue, 25% methanol, 5% glycerol) for 10 min, destained with the same fixative without toluidine blue, and then imaged in white light on a flatbed scanner.

Native Polyacrylamide Gel Electrophoresis (PAGE), Analytic Gel Filtration and Differential Scanning Fluorimetry (DSF).

Native PAGE, analytic gel filtration and DSF (also referred to as thermal shift assay)[38] were used to assess polyphosphate-protein interactions.

Native PAGE was used to assess polyP-protein interactions (known as electromobility shift assay). Mini gels were hand-cast according to Laemmli's gel system in the absence of detergent and reducing agent. 4× resolving and stacking gel buffer consisted of 1.5 M Tris-HCl (pH 8.8) and 1.0 M Tris-HCl (pH 6.8), respectively. Running buffer contained 25 mM Tris and 192 mM glycine (pH 8.3).

1-2 µg of protein was incubated with 3 µg polyP (or buffer as control) at ambient temperature for 10 min before adding sample buffer (50 mM Tris-HCl pH 6.8, 10% glycerol, 0.02% bromophenol blue). Proteins were electrophoresed at 100 V constant voltage for 2 hours, stained with EZBlue Coomassie Brilliant Blue G-250 from Sigma-Aldrich and destained with several changes of water, and then imaged in white light on a flatbed scanner.

Gel Filtration.

Proteins were stored in their stock solution buffers. The C5b,6 buffer consisted of 10 mM HEPES, 120 mM NaCl, pH 7.2. The C7 buffer consisted of 10 mM $Na_3PO_4$, 145 mM NaCl, at pH 7.3 (PBS). The buffers were filtered through a 0.22 µm pore diameter Stericup and Steritop Express™ PLUS filter from Millipore (Billerica, Mass., USA).

Proteins were thawed at 37° C. for 10 min. An excess amount of protein was removed from the stock vial and transferred to a clean 600 µL microtube. C7 was diluted to 50 µg/µl. The proteins were centrifuged at 20,817 g for 15 min and under a Class 2A Biosafety Cabinet, 100 µL fractions were transferred to clean microtubes. The following samples were analyzed by gel filtration:
(a) C5b,6 alone
(b) C5b,6 with $polyP_{1000}$
(c) C5b,6 with monophosphate ($P_1$)
(d) C7 alone
(e) C7 with $polyP_{1000}$ For all samples, 20 µg of the protein in 100 µL of their respective buffers was prepared. For samples containing polyphosphate, 8 µL of 400 mM $polyP_{>1000}$ was mixed with 2 µL of 5× concentrated HBS (for C5b,6) or PBS (for C7), yielding a solution of 320 mM $polyP_{>1000}$ in HBS or PBS. 3.13 µL of the polyphosphate solution was added to 100 µL of either C5b,6 or C7, for a final $polyP_{>1000}$ concentration of 9.71 mM. The same protocol was used for the sample containing monophosphate ($P_1$), adding 4.17 µL of the 240 mM $P_1$ solution into 100 µL of C5b,6, for a final $P_1$ concentration of 9.61 mM. Both the $polyP_{>1000}$ and $P_1$ were centrifuged at 20,817×g for 15 min prior to adding to the proteins.

The gel filtration apparatus, ÄKTAmicro System from G.E. Healthcare (Buckinghamshire, UK), was equilibrated with either HBS (0.22 µm filtered) for C5b,6 or PBS (0.22 µm filtered) for C7 for at least 1 hour, at 5 µL per minute. The column was a Superose 6 PC 3.2/30 from G.E. Healthcare (Buckinghamshire, UK). Protein was monitored with UV absorbance at 280 nm. The entire volume of each sample was injected onto the column after equilibration with buffer. Data for each curve were normalized to the point where the peak starts.

For DSF, 25 µL reaction mixes consisting of 0.4 mg/mL protein (0.14 mg/mL for C5b,6), varying concentrations of polyphosphate diluted in HBS (20 mM HEPES, 150 mM NaCl, pH 7.4), and 5× SYPRO Orange were loaded into MicroAmp Fast Optical 96-well Reaction Plates (Applied Biosystems). Samples were heat denatured in an Applied Biosystems StepOnePlus Real-Time PCR System using a ramp configuration starting at 25° C. and increasing at 1 C.° $min^{-1}$ to 95° C. Fluorescence (in relative fluorescence units, RFU) was measured every 30 seconds[38]. Data for each curve were normalized to the maximum and the minimum of the curve.

Clot Turbidity Assay.

Clot turbidity assays were performed in untreated 96-well microplates (Corning, Tewksbury, Mass., USA) that were blocked with 1% BSA overnight at 4° C. and washed before using. $PolyP_{>1000}$ was diluted in a lipid mixture containing 125 mM imidazole (pH 7.0) and 75 µM unilamellar phospholipid vesicles consisting of 20% 1,2-dioleoyl-sn-glycero-3-phospho-L-serine (DOPS) and 80% 1-palmitoyl-2-oleoyl-sn-glycero-3-phosphocholine (POPC; both from Avanti Polar Lipids, Alabaster, Ala., USA), that was freshly made using the Avestin Liposofast apparatus (Ottawa, ON, Canada) according to the manufacturer's instructions. 50 μL polyP$_{>1000}$ was incubated with 50 μL normal pooled plasma (Affinity Biologicals, Ancaster, ON, Canada) at 37° C. for 3 minutes, and clotting was initiated by adding 50 μL of 25 mM CaCl$_2$. Turbidity was measured at A405 using a SpectraMax 190 Microplate Reader (Molecular Devices, Sunnyvale, Calif., USA) every 20 seconds for 60 minutes until absorbance from all wells plateaued. Clot time was defined as the time at which the horizontal line across baseline absorbance intersects with a fitted line to the steepest linear region of the curve during clot formation.

Statistical Analyses.

Analyses were performed with GraphPad Prism version 5.0 (San Diego, Calif., USA). Where indicated, one-way ANOVA with Bonferroni's multiple comparison tests were performed. Results shown are means± standard error of the mean. Statistical significance refers to p<0.05.

Experimental Choroidal Neovascularization (CNV) Model in Rats.

Eleven-week-old female Long Even (LE) rats (Charles River Laboratory, Wilmington, Mass.) weighing 256 to 315 g were used. The animals were handled in accordance with institutional guidelines and the ARVO Statement for the Use of Animals in Ophthalmic and Vision Research. The rats were anesthetized by intramuscular injection of a 1 mL/kg mixture (1:1) of ketamine hydrochloride (40 mg/kg) and xylazine hydrochloride (10 mg/ml), and their pupils were dilated with tropicamide (0.5% Mydrin). Experimental choroidal neovascularization (CNV) was created as described previously (Takehana et al., Invest Ophthalmol Vis Sci, 1999, 40 (2):459-66). Briefly, under a slit lamp biomicroscope using a 22×22-mm coverglass as a contact lens, four to five laser photocoagulations were applied to each left eye between the major retinal vessels around the optic disk under the following conditions: power 150 mW intensity, duration 100 ms and spot size 75 um (A diode red laser (650 nm; OcuLight SLx; Iris Medical Instruments). Bruch's membrane was breached, as evidenced by visualization of a central bubble formation without intraretinal or choroidal hemorrhage.

Intraocular Injection Protocol in Rats.

After laser treatment, under anesthesia, intravitreal injections were performed on a lasered eye under a dissecting microscope (Stereo dissection microscope, SMZ 1000; Nikon, Tokyo, Japan). A fine needle (#28-needle or Insulin Syringe external diameter, 360 μm) was used to make a small puncture opening in the region of the limbus. Then a 32-gauge Hamilton needle attached to a 5-μl syringe was inserted immediately into the puncture opening and placed into the vitreous cavity. Next, 5 μl of polyphosphate (1 mM) or similar volume of monophosphate control in sterile water was slowly injected into the vitreous. The needle was left in position for 30 to 60 seconds and then slowly withdrawn to minimize fluid reflux and loss from the eye. After the procedure, animals were monitored in a recovery enclosure until they resumed baseline normal activity levels. Animals were kept for 5 days post injection and euthanasia was performed with CO$_2$ inhalation. Eyes were immediately enucleated and preserved in 4% paraformaldehyde in Dulbecco's phosphate-buffered saline.

Flatmount Technique.

24 hours after fixation, the globes were dissected under a dissecting microscope. Next, the anterior segment and crystalline lens were removed, and the neuroretinas were detached and separated from the optic nerve head with fine curved scissors. The remaining eye cups (sclera, choroid and retinal pigmented epithelium (RPE)) were washed with PBS. A 1:100 dilution of 500 ug/ml solution of fluorescein labeled Griffonia simplex lectin (GSL-IB4) was used to identify endothelial cells and a 1:250 dilution of a 1 mg/ml solution of anti-C5b-9 was used for C5b-9 immunoreactivity. After incubation in these solutions, the eye cup preparation underwent radial incisions in order to flat mount the tissue, with RPE side up. Mounting solution (VectaShield) was applied, and coverslip placed over eye cup flatmount preparation and sealed.

Confocal Imaging and Analysis.

Each eye cup flatmount preparation was analyzed using a confocal laser-scanning microscope (Zeiss-LSM 510 META). The CNV laser lesions were imaged at 20× magnification. The fields were scanned with wavelengths of 488 nm (green) and 571 nm (red wavelength). Images were exported to Adobe Photoshop for digital processing. All digital images were prepared from 1024×1024 pixel originals, with a resolution of 460×460 pixels/in. Comparative digital images from drug treated and control samples were captured using identical brightness and contrast settings. Intensity and size of GSL-IB4 and C5b-9 immunohistochemistry were analyzed using image-processing and image-analysis software Image J 1.37 (developed by Wayne Rasband, National Institute of Health, Bethesda, Md., USA).

Example 2

Polyphoshate Suppresses Total Hemolytic Activity in a Concentration-Dependent Manner The effect of polyphosphate on total complement-mediated hemolytic activity was assessed. NHS (4.5%) diluted to yield 70-80% lysis, as described herein, was pre-incubated with varying concentrations of polyphosphate having more than 1000 orthophosphate units (NaPO$_3$) per chain (polyphosphate$_{>1000}$) and that optimally promotes coagulation[14]. Orthophosphate (P$_1$), the monomeric unit of polyphosphate, was used as a control. Reactions were initiated by the addition of rRBC and hemolysis was measured after 30 min. Values were normalized to baseline lysis in the absence of phosphate. Curves were fitted to a nonlinear regression inhibitory dose-response model to determine IC$_{50}$ for P$_1$ and polyphosphate.

Figure 4:
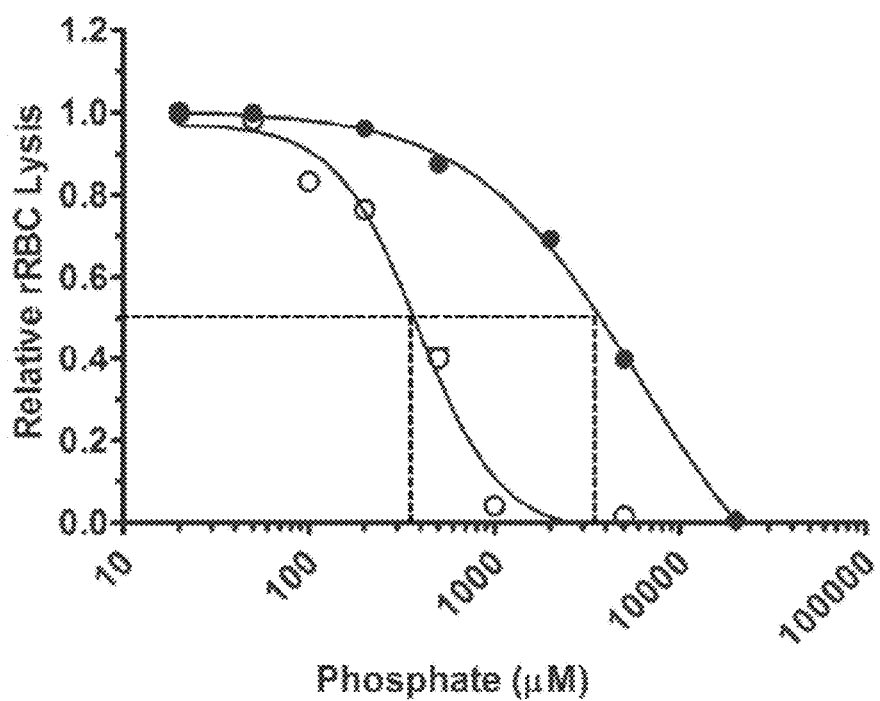
FIG. 4 is a graph showing the effect of polyphosphate on total hemolytic activity. (●) represents $P_1$ and (○) represents polyphosphate$_{>1000}$. The dotted lines represent the IC$_{50}$ for $P_1$ and polyphosphate. Results are representative of 3 experiments, each performed in triplicate.

P$_1$ and polyphosphate$_{>1000}$ both suppressed hemolysis in a concentration-dependent manner (FIG. 4). However, at equivalent molar concentrations of the monomeric form, polyphosphate$_{>1000}$ was strikingly more effective at suppressing hemolysis. The IC$_{50}$ (the concentration required to achieve half maximal inhibition of lysis) was ~3.5 mM for P$_1$ and ~350 μM for polyphosphate$_{>1000}$, shown by dotted lines.

Example 3

Polyphosphate but not Momophosphate, Suppresses Complement-Mediated Lysis Via the TP in Serum We examined the effect of polyphosphate on the TP of complement. The TP is initiated by the rapid binding of C5b to C6, and the subsequent and sequential binding of C7, C8 and several C9 molecules to form the pore-like C5b-9 MAC. This pathway is ion-independent and thus any effects of polyphosphate would also be independent of its capacity to chelate cations.

TP activity in NHS(2%), measured by lysis of cRBC, was initiated by adding a limiting amount of exogenous purified C5b,6 (250 pM) to achieve 70-80% lysis after 30 min. A molar excess of EDTA was used to prevent upstream activation of complement and generation of endogenous C5b,6. In the absence of C5b,6, there was no detectable complement-mediated cRBC lysis. $P_1$ at concentrations ranging from 0.1 to 1000 µM, had no effect on complement-mediated hemolysis in NHS via the TP (FIG. 5A). By contrast, polyphosphate$_{>1000}$ inhibited the TP in serum in a concentration-dependent manner, with an IC$_{50}$ of ~10 µM polyphosphate$_{>1000}$ (dotted lines) (calculated based on monomeric phosphate).

To verify that the effects observed were dependent on the integrity of the polyphosphate polymers, we pre-treated polyphosphate with calf intestinal alkaline phosphatase (CIAP) (400 U/mL), an exopolyphosphatase that cleaves polyphosphate into monomeric units[39], and then added to the terminal pathway assay at a final polyphosphate$_{>1000}$ concentration of 100 µM. CIAP alone had no effect on the TP hemolytic activity, whereas CIAP treatment of the 200 µM polyphosphate$_{>1000}$ completely abrogated its ability to dampen hemolytic activity via the TP (FIG. 5B).

In addition, co-incubation of up to 2 mM $P_1$ in combination with polyphosphate$_{>1000}$ at a concentration of 200 µM, added singly or in combination in the terminal pathway assay, had no effect on the suppressive properties of the polyphosphate$_{>1000}$ (FIG. 5C), indicating that excess monomer could not overcome suppressive properties of polyphosphate.

Example 4

Suppression of TP Hemolytic Activity is Dependent on the Chain Length of Polyphosphate (PolyP)

Figure 6A:
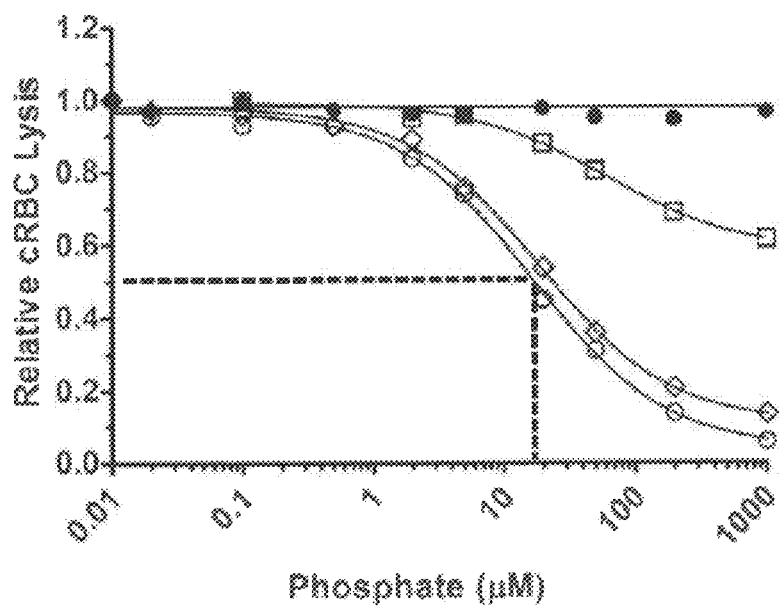
FIGS. 6A-B are graphs showing the effect of the size of the polyphosphate polymer on the terminal pathway. 6A: (●) represents $P_1$, (□) represents polyphosphate$_{<30}$, (◇) represents polyphosphate$_{40-160}$, and (○) represents polyphosphate$_{>1000}$. The dotted lines represent the IC$_{50}$ for polyphosphate. Results are representative of 3 experiments, each performed in triplicate.
Figure 6B:
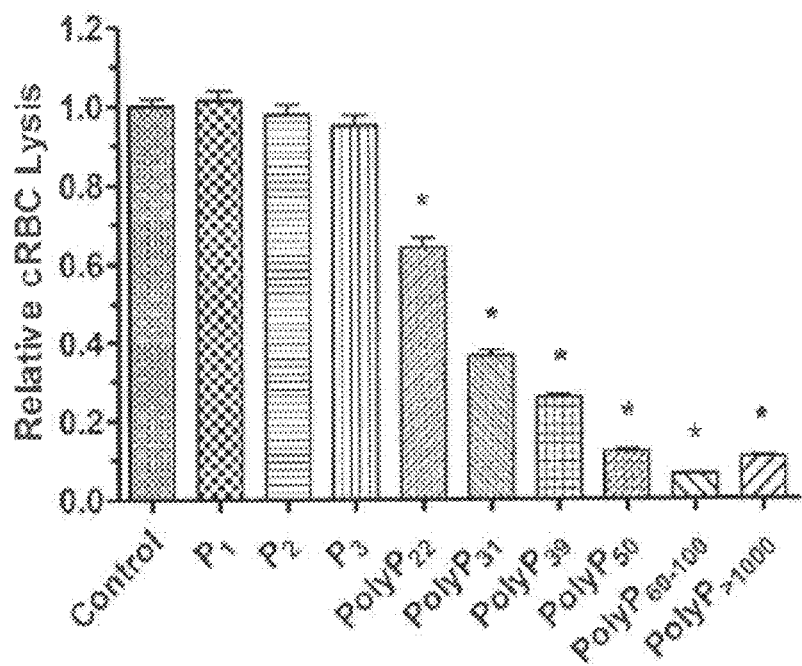

The effects of polyphosphate on coagulation are dependent on chain length. We therefore tested whether polyphosphate of different chain lengths could suppress TP hemolytic activity. $P_1$, polyP$_{<30}$, polyP$_{40-60}$, and polyP$_{>1000}$ were titrated into the terminal pathway assay in the presence of 2% serum and 250 pM C5b,6. Medium chain length polyphosphate (polyP$_{40-160}$) had a similar concentration-dependent suppressive effect as polyP$_{>1000}$ on TP mediated hemolysis (FIG. 6A). However, shorter length polyphosphate (polyP$_{<30}$) was less potent, and an IC$_{50}$ could not be achieved even with 5 mM polyP$_{<30}$. Accordingly, a wider range of different polyphosphate chain lengths was examined for effects on the TP. At equivalent 100 µM concentrations (based on the monomeric form), $P_1$, diphosphate (Na$_4$P$_2$O$_7$) (P$_2$) and triphosphate (Na$_5$P$_3$O$_{10}$) (P$_3$) had no effect on TP hemolytic activity (FIG. 6B). However, polyphosphate with a mean length of 22 orthophosphate units (polyP$_{22}$), significantly dampened TP hemolytic activity, and the extent of suppression by longer-chain polyphosphate increased in a size-dependent manner (FIG. 6B).

Example 5

Polyphosphate Depends on Early TP Components to Suppress Lytic Activity

Figure 7:
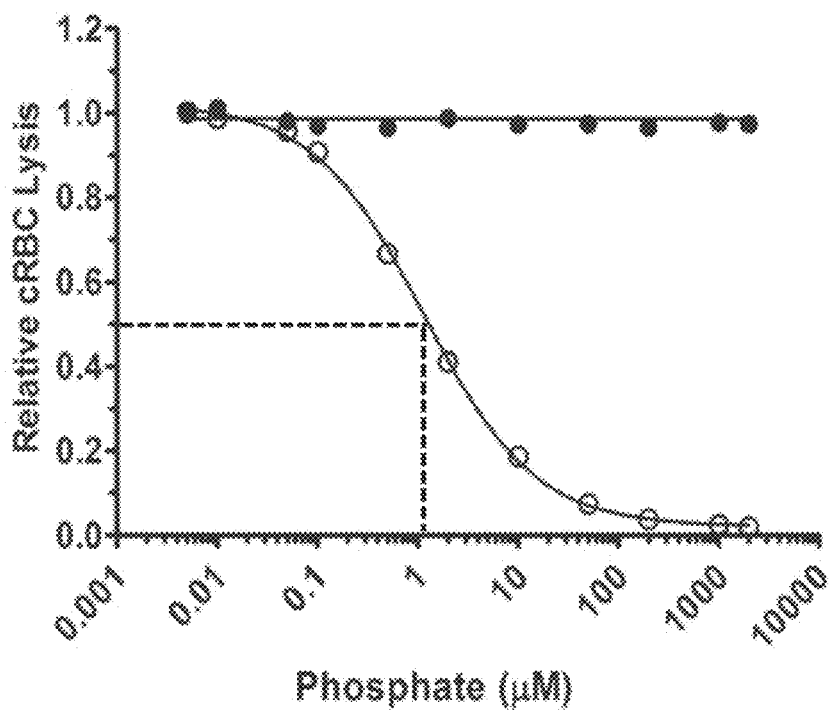
FIG. 7 is a graph showing the effect of polyphosphate on the function of terminal pathway components. (●) represents $P_1$ and (○) represents polyphosphate$_{>1000}$. The dotted lines represent the IC$_{50}$ for polyphosphate. Results are representative of 3 experiments, each performed in triplicate.

We examined whether polyphosphate suppresses TP hemolytic activity through direct interaction(s) with TP complement components (C5b,6, C7, C8, or C9) or if other serum factors are also required. This was achieved by replacing NHS with purified TP components C7, C8 and C9 as the source of complement. TP hemolytic activity in this purified system was measured by sequentially adding cRBC, varying concentrations of polyphosphate, and then purified C5b,6, C7, C8, and C9. Similar to the findings with serum, polyphosphate dose-dependently suppressed erythrocyte lysis, while $P_1$ had no effect (FIG. 7). The IC$_{50}$ of polyphosphate$_{>1000}$ (○) in this assay system was ~1 µM. The effect of polyphosphate was not specific to the species of the target erythrocytes, because TP hemolytic activity could also be suppressed by polyphosphate when human erythrocytes were used. Overall, the findings indicate that polyphosphate interferes with TP complement-mediated lysis of RBC by binding directly to one or more of the TP complement components or to the target red cell membrane.

Example 6

Figure 8:
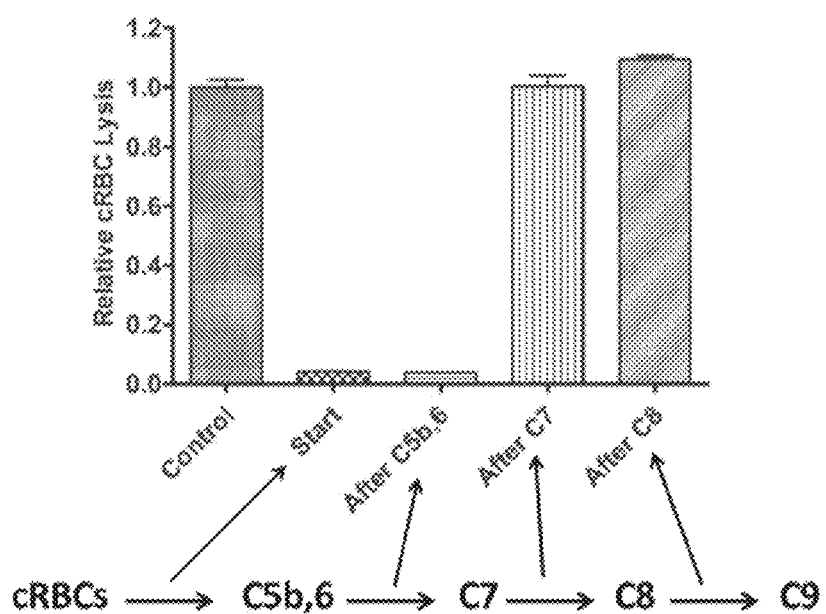
FIG. 8 is a graph showing the effect of polyphosphate on the function of terminal pathway components. Each column represents quadruplicate data points.

Polyphosphate Interferes with TP Hemolytic Activity at Early Steps in Assembly of the MAC We delineated the step(s) in the TP at which polyphosphate interferes with the function of the MAC to lyse erythrocytes. This was achieved by performing the TP assay in which polyphosphate was added at different steps of the reaction, i.e., before C5b,6, after C5b,6, after C7, after C8, or simultaneously with C9. Polyphosphate$_{>1000}$ at a concentration of 200 µM, suppressed lysis to <5% of maximal lysis (i.e. without the addition of polyphosphate), when added prior to or immediately after C5b,6 (FIG. 8). By contrast, polyphosphate had no effect on cRBC lysis in the TP assay when added after C7, after C8 or with C9 (FIG. 8). Values were normalized to baseline lysis in the control condition without the addition of polyphosphate. Relative lysis between control, after C7, and after C8 conditions were not statistically significant (p>0.05). Equivalent results were obtained with polyphosphate$_{60-100}$. The findings indicate that polyphosphate interferes with optimal MAC function/assembly by destabilizing C5b,6, limiting normal C5b,6 interaction with C7, or causing further downstream TP complexes (C5b-7, C5b-8 or C5b-9) to be unstable or incapable of attaching or inserting into the RBC membrane. Once C5b-7 forms, however, polyphosphate can no longer modulate the function of the MAC.

To determine whether polyphosphate interferes with incorporation of the terminal complex onto or into the membrane of cRBCs, we added varying concentrations of polyphosphate to the cells, followed by a 5 minute incubation with equimolar concentrations of purified C5b,6, C7, and C8. Under these conditions, the C5b-8 complex integrates into the membrane, causing minimal lysis. Cells were pelleted and the amount of unbound C5b, reflecting unbound C5b-8 complex, was assessed by Western immunoblot. More C5b was recovered in the supernatant when polyphosphate was included and this effect was dose-dependent. In a similar manner, by incubating C5b,6 and C7 (without C8 or C9), we determined that the presence of polyphosphate reduced binding of the C5b-7 complex to the erythrocyte membrane. The findings indicate that polyphosphate interferes with binding/integration of the C5b-7 and C5b-8 complexes to/into the cell membrane.

Example 7

Polyphosphate (Polyp) Alters the Stability of C5b,6 and C6 but not C5 or C7

Using independent approaches, we investigated whether polyphosphate interacts directly with different components of the TP and whether it alters the stability and thus, the function of these components.

In one approach, native PAGE was used to assess polyphosphate-protein binding. More specifically, 2 µg of protein were incubated with or without 6 µg polyP$_{>1000}$ and resolved by native PAGE. The gel was stained with Coomassie blue for detection. The results indicated that C5b,6, C6 and C7 all exhibited band shifts in the presence of polyphosphate, consistent with a physical interaction under the experimental conditions, similar to thrombin's interaction with polyphosphate (FIG. 9). Platelet derived polyphosphate does not bind to prothrombin (II)[13], as shown in FIG. 9.

In another approach, we performed gel filtration studies with either C5b,6 or C7 in the presence or absence of polyP$_{>1000}$ (10 mM). Polyphosphate had no effect on the chromatogram for C7 (FIG. 10A). This result was somewhat surprising, given the gel shift data but is likely attributable to different buffer conditions. Notably, co-incubation of polyphosphate caused a dramatic shift to a higher oligomerized state in the C5b,6 elution profile (FIG. 10B), indicating a direct interaction of C5b,6 with polyphosphate. The broader C5b,6-polyphosphate peak is consistent with polyphosphate destabilizing C5b,6. In the absence of C6, C5b is highly unstable and aggregates[40] and thus 5b and C6 were not independently examined. P$_1$ (monoP) (10 mM) did not affect the retention time or elution profile of C5b,6.

In another approach, differential scanning fluorimetry (DSF) was used to determine the thermal stability of the complement proteins in the presence and absence of polyphosphate. This technique involves heat-denaturing proteins and exposing internal hydrophobic regions to the aqueous environment, which are detected by the fluorescent dye SYPRO Orange[38]. Interactions between a protein and a binding partner often change the thermal stability of the protein, observed as a shift in the melting (denaturation) curve. C5b,6, C5, C6, and C7 were individually incubated with a range of concentrations of polyphosphate$_{>1000}$ and relative fluorescence (RFU) was measured as the proteins were thermally denatured. An increase in RFU indicates protein denaturation.

Figure 12:
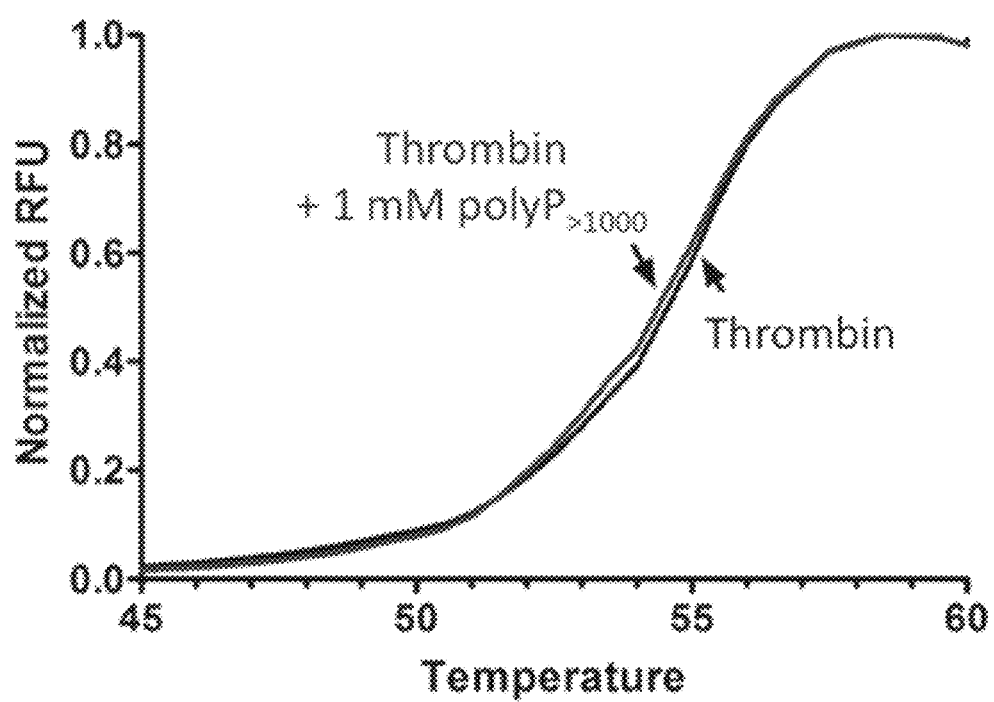
FIG. 12 is a graph showing the effect of polyphosphate on the stability of thrombin.

In the absence of polyphosphate, the melting curve of C5b,6 (FIG. 11A) is characterized by three transition phases (arrows), likely due to differential thermal stabilities between C5b,6 domains. When C5b,6 was incubated with polyphosphate$_{>1000}$, a dose-dependent leftward shift in the second transition phase at 59.5° C. was observed (boxed region from FIG. 11A expanded in FIG. 11B), strong evidence that polyphosphate binds to a distinct domain on C5b,6. The lines from FIG. 11A are labeled with the different concentrations of polyphosphate (from 0 (control) to 2 mM). Polyphosphate had no effect on the melting curve of C5, but did cause a dose-dependent destabilization shift in the C6 melting curve (FIGS. 11C and 11D, respectively), suggesting that polyphosphate interacts with C5b,6 via C6. In spite of the gel shift showing an interaction between polyphosphate and C7, only a minimal polyphosphate-induced shift in the C7 curve was observed, and only in the presence of a high concentration (1 mM) of polyphosphate (FIG. 11E). In a similar manner, although thrombin binds to polyphosphate with a K$_D$~5 nM[13], we also did not detect a polyphosphate-induced change in thrombin's thermal stability as measured by DSF. Thrombin was incubated with a range of concentrations of polyP$_{>1000}$ and relative fluorescence (RFU) was measured as the proteins were thermally denatured. In spite of the finding that thrombin binds to polyphosphate and, in contrast to the effect of polyphosphate on C5b,6, polyphosphate has no effect on the stability of thrombin (1 µM), i.e., there is no shift in the curve even with a high concentration of polyphosphate (1 mM) (FIG. 12). PolyP$_{60-100}$ had the same effect as polyP$_{>1000}$ for all proteins tested. The addition of 1 mM monophosphate (P$_1$) had no effect on the thermal stability.

Example 8

Measuring Effect of Polyphosphate (polyP) on C5b-8 and C5b-7 Binding to Erythrocyte Membranes Chicken erythrocytes (cRBC) (Colorado Serum Company, Denver, Colo.) were washed four times with gelatin veronal buffer (GVB), and resuspended in GVB at a final concentration 3.00×10$^9$ cells/mL. Varying concentrations of polyphosphate from 0 µM to 10 mM were added to the cells and incubated for 5 minutes at room temperature. C5b,6 was then added to the reaction mixtures (final concentration 2.5 nM) and incubated for 5 minutes. Finally, C7 and C8 or C7 were added at final concentrations of 2.5 nM each and incubated for a further 5 minutes. C (control) represents the condition to which results were normalized, i.e., where polyphosphate 10 mM was incubated with cRBC and C5b,6, but no C7 or C8 was added. The cells were then pelleted at 300 g for 3 minutes and 40 µL of the supernatant was transferred to another microfuge tube. This was again centrifuged at 300 g for 3 minutes to remove any contaminating cRBC. 32 µL of this supernatant containing any unbound complement components was mixed with 8 µL of Laemmli buffer with beta-mercaptoethanol for separation by SDS-PAGE on a 10% acrylamide gel. The transferred gel was Western immunoblotted with goat-anti-human C5 primary antibody (Complement Technology, Inc. Tyler, Tex.) with detection accomplished with 680RD donkey-anti-goat secondary antibody from LI-COR Biosciences (Lincoln, Nebr.). The α'-chain of C5b was quantified by densitometry using the Odyssey Software from LI-COR Biosciences (Lincoln, Nebr.). Values were normalized to the experimental conditions in which cRBC were incubated with maximal concentrations of polyP, but without C7 or C8. The amount of C5b under these conditions was considered to be 100%.

The results indicated that polyP reduces the ability of C5b-7 and C5b-8 to attach and integrate into the red cell membrane, thereby reducing effective generation of the C5b-9 MAC.

Example 9

Polyphosphate$_{>1000}$ (PolyP$_{>1000}$) Shortens Plasma Clotting Time

Figure 14:
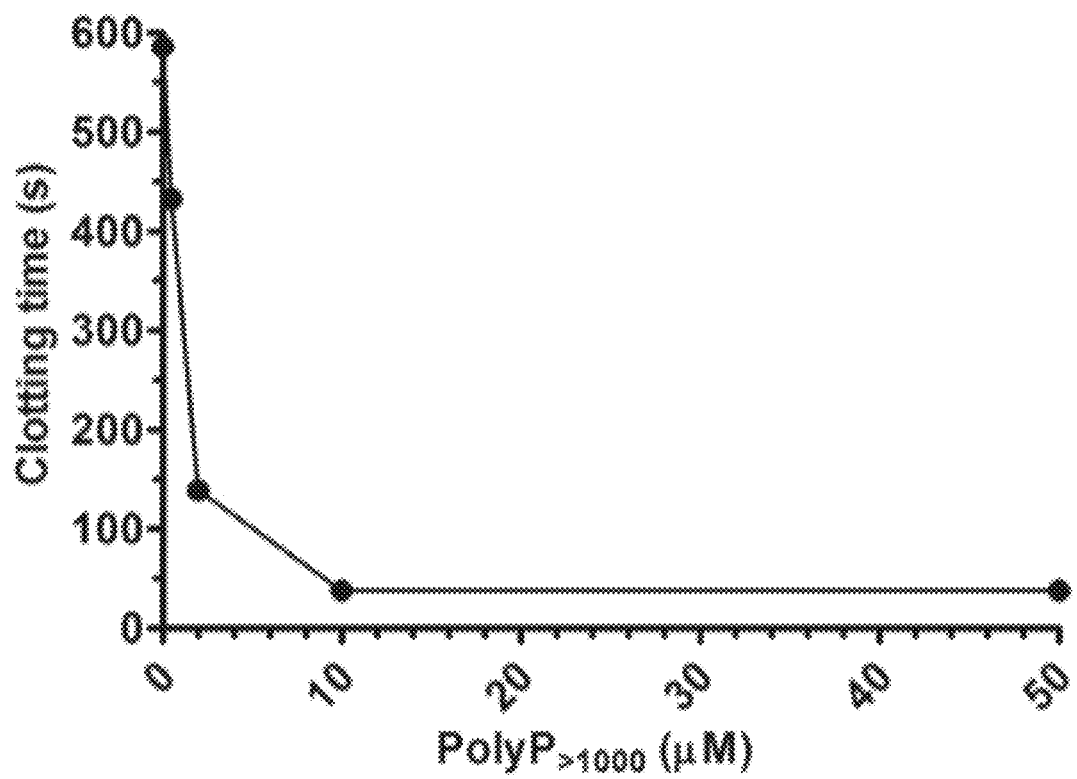
FIG. 14 is a graph showing the effect of polyphosphate on plasma clotting time.

Clot turbidity assays were performed in untreated 96-well microplates with a range of polyP$_{>1000}$ co-incubated with plasma. The results indicated that the clotting time is dramatically shortened with low concentrations of polyP$_{>1000}$ (FIG. 14).

Example 10

Polyphosphate Augments Inhibitory Properties C1-Esterase Inhibitor (C1-Inh) to Dampen Complement Activation We tested whether polyP affects the inhibitory properties of C1-inh on C1s-mediated cleavage and activation of complement factor C4 and C2. SDS-PAGE followed by coomassie staining of gels was used to monitor cleavage of C4 by C1s in the presence/absence of C1-inh and/or polyP in a purified system.

Absence of C1-Inh.

Figure 15A:
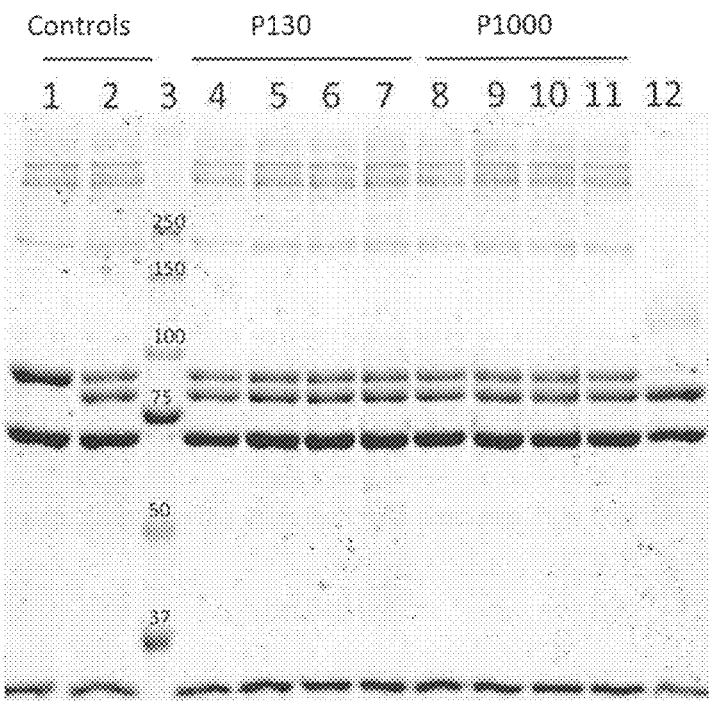
FIGS. 15A-B are photographs of gels showing the effect of polyphosphate on C4 cleavage by C1s in the absence (A) and presence (B) of C1-inh. 15A: The controls are C4 (lane 1) and C4+C1s (lane 2). Lanes 4-7 are C4+C1s with increasing concentrations of polyP$_{130}$ (25 μM, 50 μM, 100 μM and 300 μM). Lanes 8-11 are C4+C1s with increasing concentrations of polyP$_{1000}$ (25 μM, 50 μM, 100 μM and 300 μM). Lane 12 is C4b. 15B: The controls are C4 (lane 1), C4+C1s (lane 2), C4+C1s+2.5 nM C1-inh (lane 3) and C4+C1s+25 nM C1-inh (lane 4). Lanes 6 and 7 (reaction 1): C4+C1s with 2.5 nM and 25 nM of C1-inh, respectively, with polyP$_{130}$. Lanes 8 and 9 (reaction 2): C4+C1s with 2.5 nM and 25 nM of C1-inh, respectively, with polyP$_{130}$. Lanes 10 and 11 (reaction 1): C4+C1s with 2.5 nM and 25 nM of C1-inh, respectively, with polyP$_{1000}$. Lanes 12 and 13 (reaction 2): C4+C1s with 2.5 nM and 25 nM of C1-inh, respectively, with polyP$_{1000}$.

2.5 nM C1s and 25-300 μM polyP (P) were incubated in 20 mM Hepes, 0.15 M NaCl, pH 7.5, 0.01% Tween buffer for 90 minutes at 37° C. 1.5 μM C4 was added and incubated for 5 minutes at 37° C. The reactions were quenched with 5× loading buffer and β-ME. Samples were taken and run on an SDS-PAGE 8% gel (FIG. 15A). The results indicated that, in the absence of C1-inh, polyP had no effect on C1s-mediated cleavage of C4.

Presence of C1-Inh.

Figure 15B:
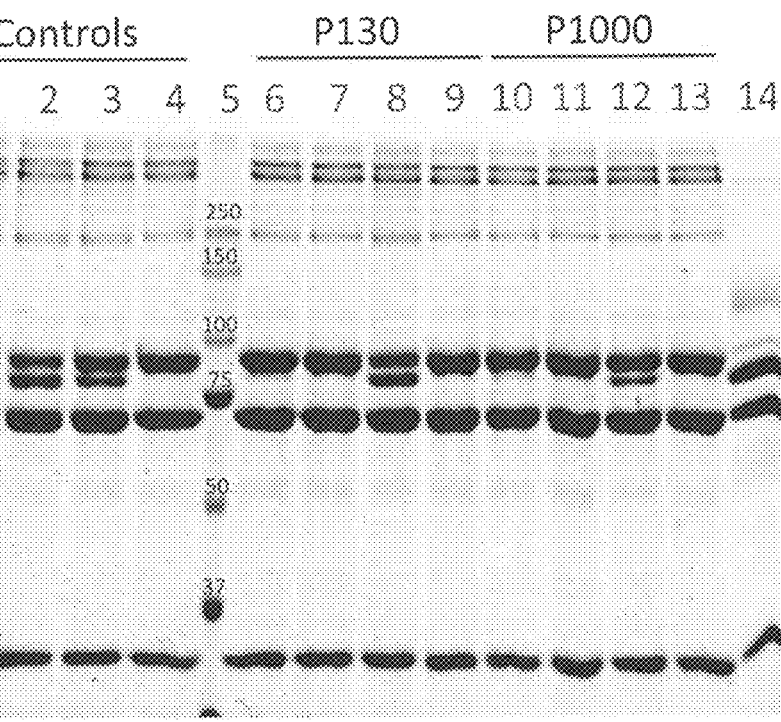

2.5 nM C1s (reaction 1) or 2.5 nM C1-inh (reaction 2), and 300 μM polyP were incubated in 20 mM Hepes, 0.15 M NaCl, pH 7.5, 0.01% Tween buffer for 90 minutes at 37° C. 2.5 nM C1-inh (reaction 1) or 0.5 nM C1s (reaction 2) was added and incubated for 30 minutes at 37° C. 1.5 μM C4 was added and incubated for 5 minutes at 37° C. The reactions were quenched with 5× loading buffer and β-ME. Samples were taken and run on an SDS-PAGE 8% gel (FIG. 15B). The results indicated that preincubation of polyP of lengths 130 (polyP$_{130}$) or >1000 (polyP$_{1000}$) with C1s, followed by addition of C1-inh and C4, resulted in reduced cleavage of C4 by C1s.

Figure 16A:
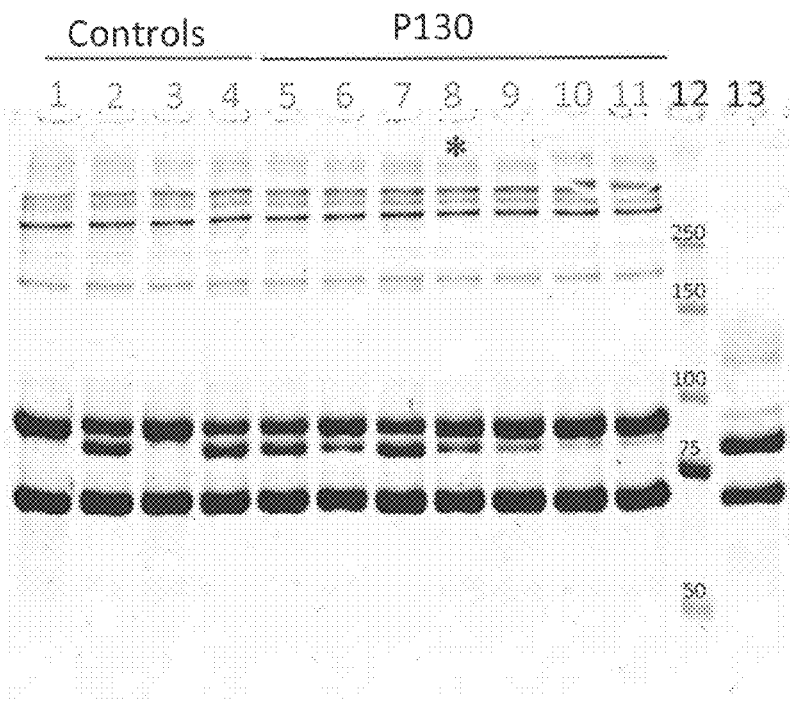
FIGS. 16A-B are photographs of gels showing the effect of polyphosphate dosage on C4 cleavage by C1s in the presence of C1-inh. The controls are C4 (lane 1), C4+C1s (lane 2), C4+C1s+25 nM C1-inh (lane 3) and C4+C1s+2.5 nM C1-inh (lane 4). Lanes 13 are C4b. 16A: Lanes 5-11 (reaction 1): C4+C1s+2.5 nM C1-inh with increasing concentrations of polyP$_{130}$ (5 μM, 10 μM, 25 μM, 50 μM, 100 μM, 200 μM and 300 μM). 16B: Lanes 5-11 (reaction 2): C4+C1s+2.5 nM C1-inh with increasing concentrations of polyP$_{1000}$ (5 μM, 10 μM, 25 μM, 50 μM, 100 μM, 200 μM and 300 μM).
Figure 16B:
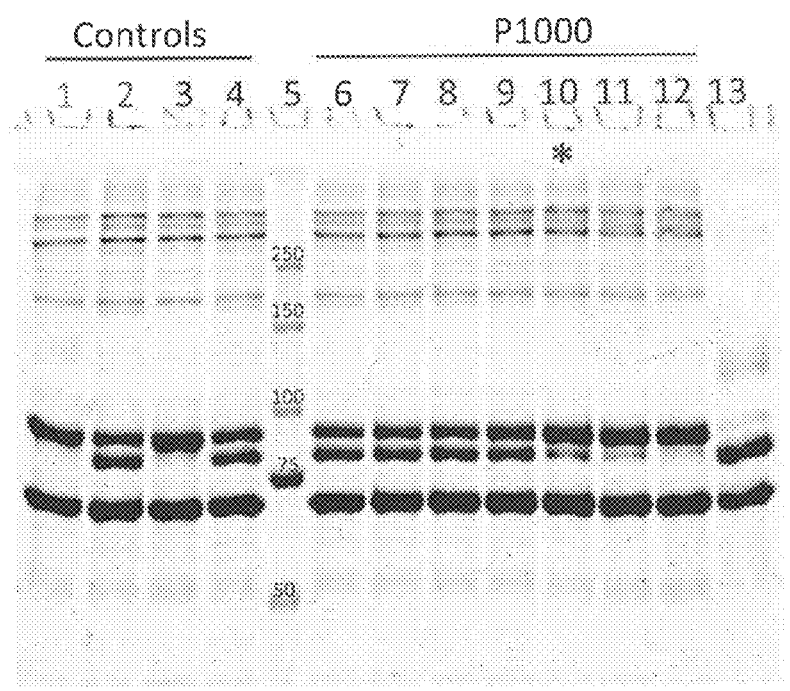

This effect of polyP was concentration dependent, with higher concentrations being more effective at enhancing the inhibitory properties of C1-inh (FIGS. 16A, B). Briefly, 2.5 nM C1s with 5-300 μM of polyP$_{130}$ (reaction 1; FIG. 16A) or polyP$_{1000}$ (reaction 2; FIG. 16B) were incubated in 20 mM Hepes, 0.15 M NaCl, pH 7.5, 0.01% Tween buffer for 90 minutes at 37° C. 2.5 nM C1s was added and incubated for 30 minutes at 37° C. 1.5 μM C4 was added and incubated for 5 minutes at 37° C. The reactions were quenched with 5× loading buffer and β-ME.

PolyP as small as P$_{14}$ enhanced the effect of C1-inh (FIGS. 17A, B). Briefly, 2.5 nM C1s with 10-500 μM of polyP$_{14}$, polyP$_{60}$, polyP$_{130}$, polyP$_{1000}$ were incubated in 20 mM Hepes, 0.15 M NaCl, pH 7.5, 0.01% Tween buffer for 90 minutes at 37° C. 2.5 nM C1s was added and incubated for 30 minutes at 37° C. 1.5 μM C4 was added and incubated for 5 minutes at 37° C. The reactions were quenched with 5× loading buffer and β-ME.

Figure 18:
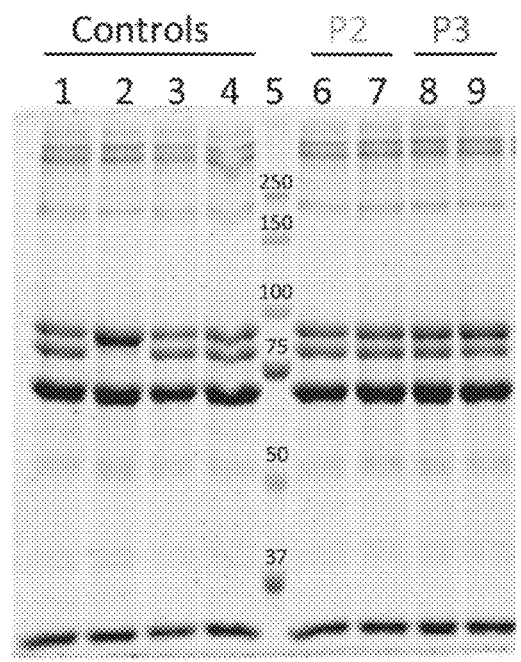
FIG. 18 is a photograph of a gel showing the effect of polyphosphate size on C4 cleavage by C1s in the presence of C1-inh. The controls are C4+C1s (lane 1), C4+C1s+25 nM C1-inh (lane 2), C4+C1s+2.5 nM C1-inh (lane 3), and C4+C1s+2.5 nM C1-inh+250 μM Na$_3$PO$_4$ (lane 4). Lanes 6 and 7 are C4+C1s+2.5 nM C1-inh with decreasing concentrations of polyP$_2$ (250 μM and 50 μM). Lanes 8 and 9 are C4+C1s+2.5 nM C1-inh with decreasing concentrations of polyP$_3$ (250 μM and 50 μM).

PolyP that were P$_2$ and P$_3$ however had no effect on C1-inh (FIG. 18). Briefly, 2.5 nM C1s with 10-500 μM of polyP$_2$ or polyP$_3$ were incubated in 20 mM Hepes, 0.15 M NaCl, pH 7.5, 0.01% Tween buffer for 90 minutes at 37° C. 2.5 nM C1s was added and incubated for 30 minutes at 37° C. 1.5 μM C4 was added and incubated for 5 minutes at 37° C. The reactions were quenched with 5× loading buffer and β-ME.

Figure 19:
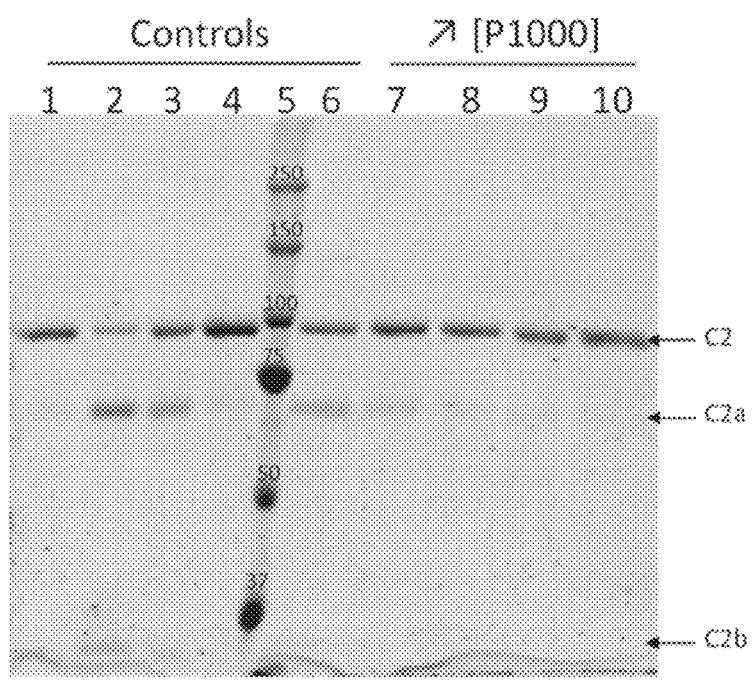
FIG. 19 is a photograph of a gel showing the effect of polyphosphate on C2 cleavage by C1s in the presence of C1-inh. Controls are C4 (lane 1), C2+C1s (lane 2), C2+C1s+5 nM C1-inh (lane 3) and C2+C1s+200 nM C1-inh (lane 4). Lane 6 is C2+C1s+C1-inh+500 μM P$_1$. Lanes 7-10 are C2+C1s+C1-inh with increasing concentrations of polyP$_{1000}$ (100 μM, 200 μM, 300 μM and 500 μM).

We also determined that polyP$_{1000}$ augments the activity of C1-inh in interfering with C1s-mediated cleavage of C2 (FIG. 19) in a concentration-dependent manner, whereas P$_1$ had no effect. Briefly, 6 nM C1s with 10-500 μM of polyP$_{1000}$ were incubated in 20 mM Hepes, 0.15 M NaCl, pH 7.5, 0.01% Tween buffer for 90 minutes at 37° C. 5 nM C1-inh was added and incubated for 30 minutes. C2 was added and incubated for 5 minutes at 37° C. The reactions were quenched with 5× loading buffer and β-ME.

Figure 20:
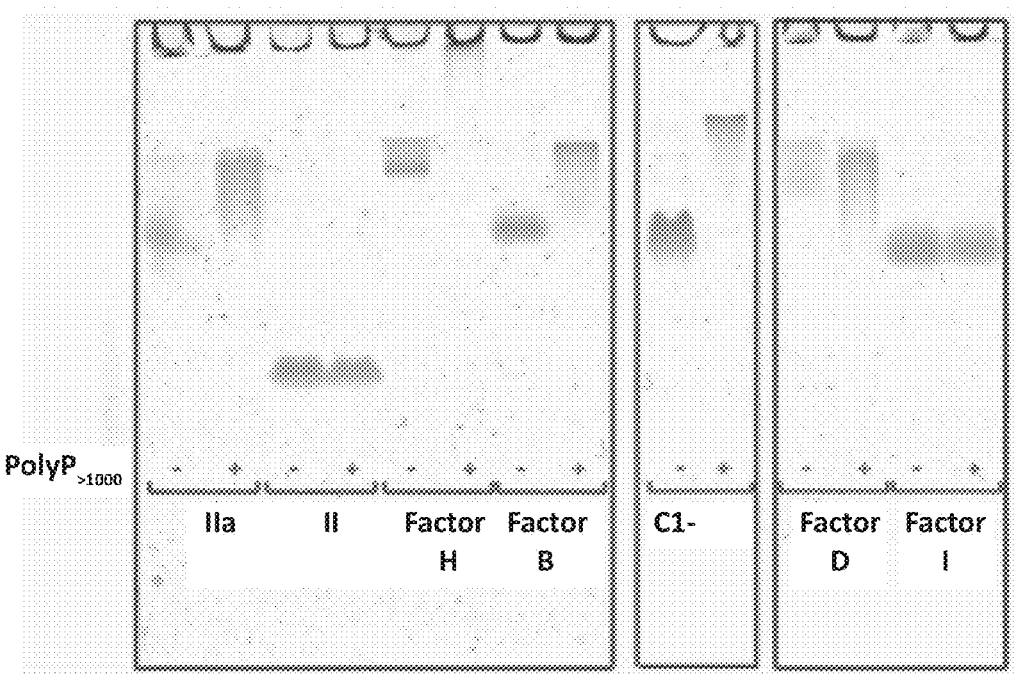
FIG. 20 is a photograph of a gel showing the effect of polyphosphate on the electromobility of thrombin (IIa), factor H, factor B, C1-inh, prothrombin (II), factor D and factor I.

We determined that polyphosphate binds to factor H, factor B and C1-esterase inhibitor (C1-inh). 2 μg of protein were incubated with or without 6 μg polyP$_{>1000}$ and resolved by native PAGE. The gel was stained with Coomassie blue for detection. Polyphosphate binds to and causes a shift in the migration of thrombin (IIa), factor H, factor B and C1-esterase inhibitor (C1-inh), but does not affect migration of prothrombin (II), factor D or factor I (FIG. 20).

Example 11

Using cultured cell lines as models of choroidal endothelial cells (CEC; RF/6A)[73] and retinal pigmented epithelial cells (ARPE-19)[74], we tested whether polyphosphate (polyP) could protect against stress-induced alterations in cell survival and deposition of terminal complement activation products (C5b-9).

Figure 21A:
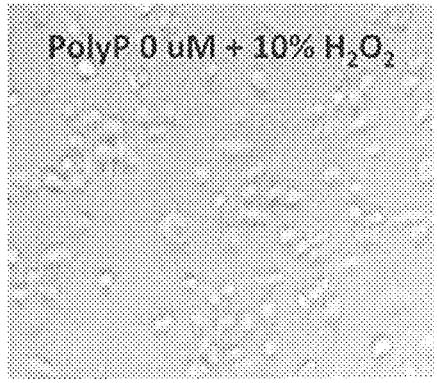
FIGS. 21A-B are photographs of CEC cells showing the effect of polyphosphate on oxidative stress. A: 0 μM PolyP, 10% H$_2$O$_2$. B: 500 μM PolyP, 10% H$_2$O$_2$.
Figure 21B:
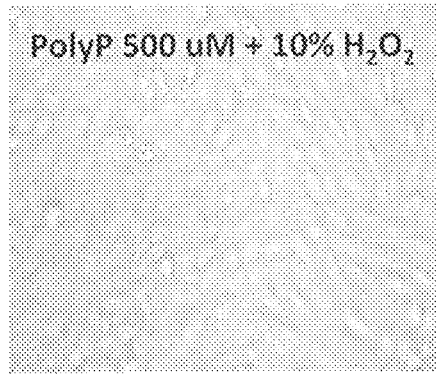
Figure 22A:
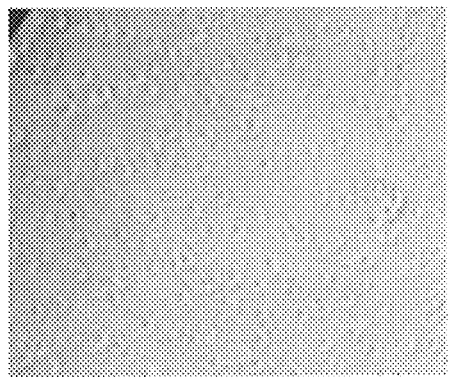
FIGS. 22A-B are photographs of ARPE cells showing the effect of polyphosphate on oxidative stress. A: 0 μM PolyP, 10% H$_2$O$_2$. B: 500 μM PolyP, 10% H$_2$O$_2$.
Figure 22B:
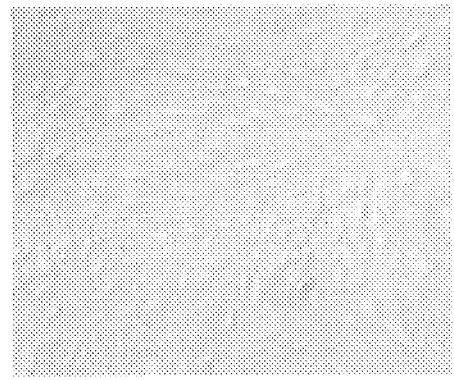

PolyP Protects Cells Against Oxidative Stress:

CEC (FIG. 21) or ARPE-19 (FIG. 22) cells were grown to ~80% confluence in DMEM+10% serum, and then incubated with varying concentration of hydrogen peroxide (H$_2$O$_2$) for 24 hours in the presence of varying concentrations of polyP$_{1000}$. As seen by direct visualization by microscopy, exposure to the oxidative stress clearly reduced the number of cells and caused them to become rounded (FIGS. 21A and 22A). A range of concentrations of polyP$_{>1000}$, from 100 μM to 1000 μM, was tested and a concentration-dependent protective effect was observed. Full protection was noted when cells were exposed to 10% H$_2$O$_2$ in the presence of 200 uM polyP$_{1000}$ (FIGS. 21B and 22B). No effect was observed with P$_1$.

Figure 23:
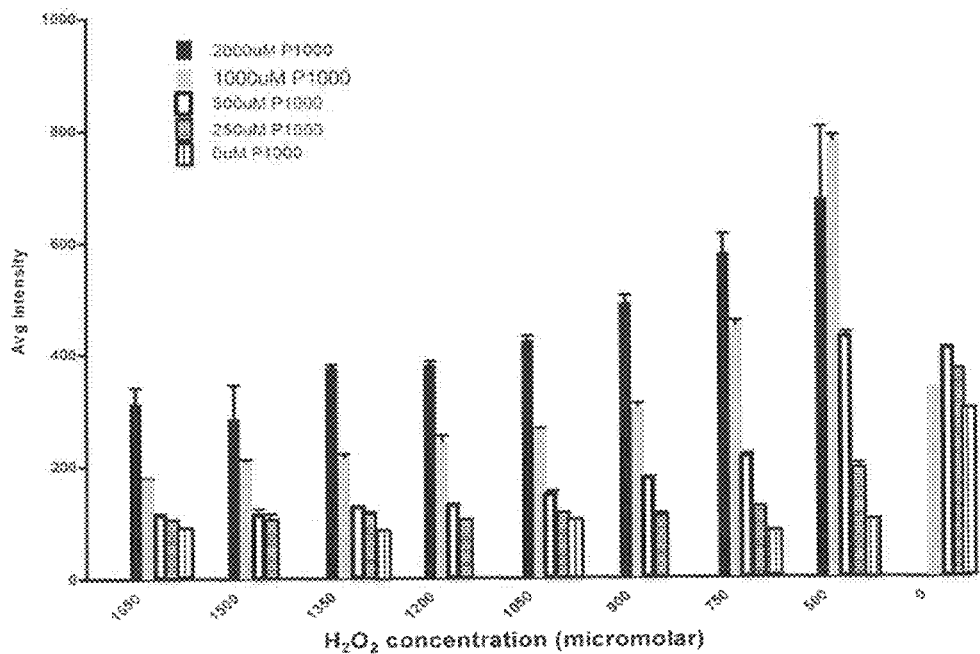
FIG. 23 is a graph showing the effect of polyphosphate on the oxidative stress in CEC cells.

We also quantified the number of live cells (CEC) using Hoechst staining in response to 24 hours exposure to H$_2$O$_2$ at a range of concentrations, in the presence of different concentrations of polyP$_{1000}$ (FIG. 23). For each concentration of H$_2$O$_2$, the bars represent, from left to right, 2000 μM, 1000 μM, 500 μM, 250 μM and 0 μM of polyP$_{1000}$. The results indicated that polyP$_{1000}$ protects cells from H$_2$O$_2$-induced death in a concentration-dependent manner.

Figures 24A, 24B, 24C:
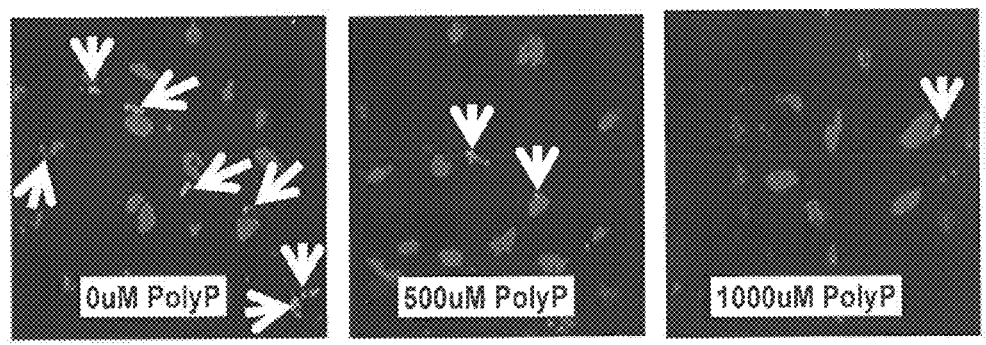
FIGS. 24A-C are photographs of CEC cells showing the effect of polyphosphate on the deposition of C5b-9 on cells. Red fluorescence (indicated with arrows) for C5b-9; blue DAPI staining for nuclei.
Figure 25:
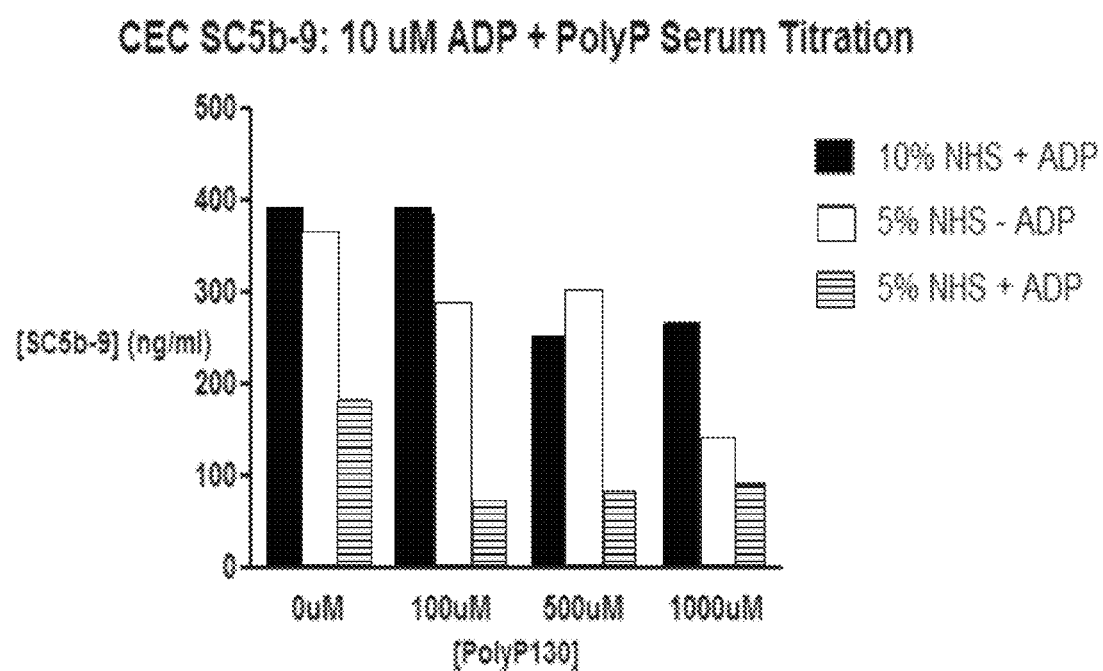
FIG. 25 is a graph showing the effect of polyphosphate on soluble C5b-9. For each concentration of polyP$_{130}$, the bars represent, from left to right, 10% NHS+ADP, 5% NHS-ADP and 5% NHS+ADP.

PolyP Reduces C5b-9 Deposition on Cells Exposed to ADP:

After serum starvation for 24 hours, CEC were exposed to 10 micromolar ADP for 10 minutes, washed and then exposed to varying concentrations of normal human serum (0, 5%, 10%) for 1 hour, in the presence of varying concentrations of polyP$_{130}$. The media was then collected and the cells were fixed and stained for deposition of C5b-9. PolyP$_{130}$ suppressed deposition of C5b-9 on the cell surface (FIGS. 24A-C) in a concentration dependent manner. Soluble C5b-9 (sC5b-9) in the media was quantified by ELISA, and it was determined that polyP$_{130}$ also suppressed the levels in a concentration dependent manner (FIG. 25). Similar findings were obtained with ARPE-19 cells that were treated in the same manner as the CEC above. These results are consistent with polyP having the capacity to reduce complement activation on the cell surface, thereby protecting the cells from damage associated with inflammation or other complement-mediated diseases.

Figure 26:
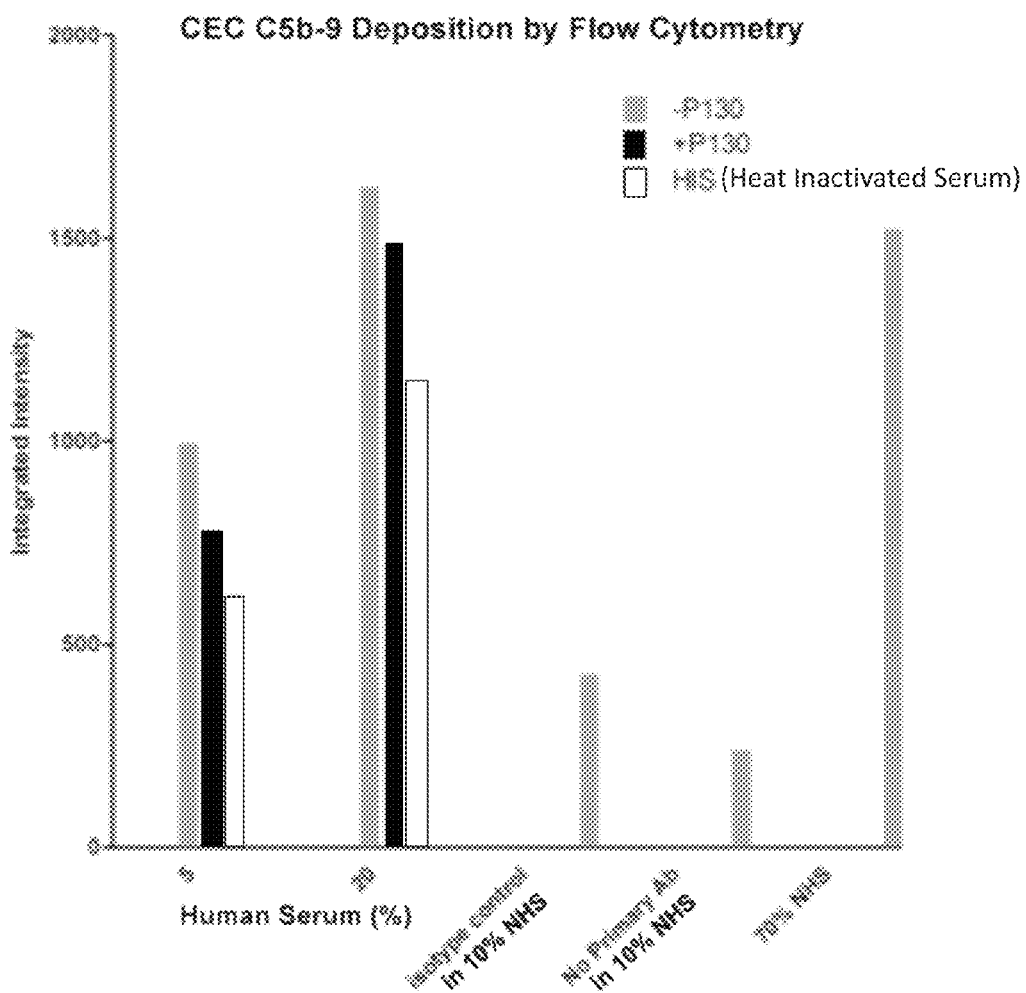
FIG. 26 is a graph showing the effect of polyphosphate on C5b-9 deposition on CEC cells. For each % of human serum, the bars represent, from left to right, −polyP$_{130}$, +polyP$_{130}$ and Heat Inactivated Serum (HIS). Isotype control in 10% NHS, untreated in 10% NHS, and 70% NHS are −polyP$_{130}$.
Figure 27:
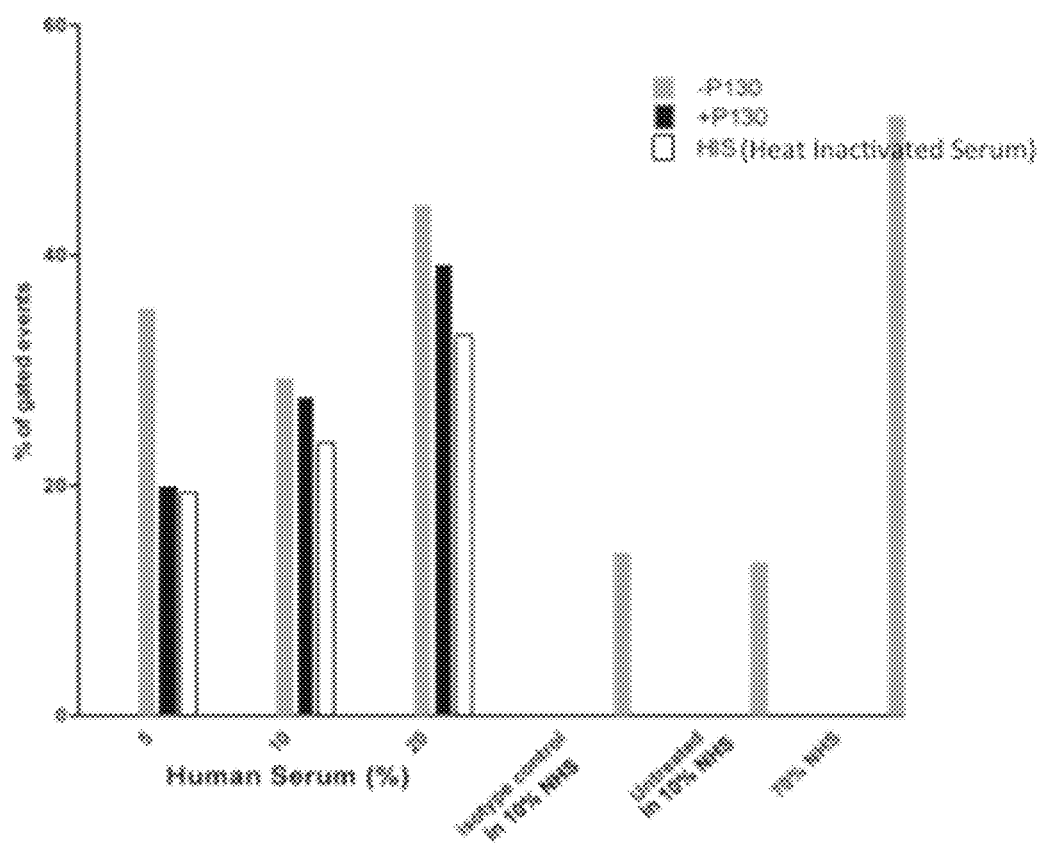
FIG. 27 is a graph showing the effect of polyphosphate on C5b-9 deposition on ARPE-19 cells. For each % of human serum, the bars represent, from left to right, −polyP$_{130}$, +polyP$_{130}$ and Heat Inactivated Serum (HIS). Isotype control in 10% NHS, untreated in 10% NHS, and 70% NHS are −polyP$_{130}$.

PolyP Protects CEC from Deposition of C5b-9 Following Exposure to High Concentrations of Normal Human Serum:

After serum starvation for 24 hours, CEC (FIG. 26) and ARPE-19 cells (FIG. 27) were exposed to increasing concentrations of normal human serum (NHS) from for 1 hour, in the presence of different concentrations of polyP$_{130}$, at the end of which, deposition of C5b-9 on the cell surface was assessed by flow cytometry. Baseline non-specific signal level was determined by using an isotype matched antibody with 10% NHS. Increasing concentrations of NHS from 5-20% yielded a greater amount of C5b-9 deposition. polyP$_{130}$ at a concentration of 100 uM significantly reduced the amount of C5b-9 deposited on the cell surface (CEC and ARPE-19 cells). The results are consistent with polyP having the capacity to dampen complement activation on the cell surface, thereby protecting the cells from damage.

Example 12

Whole Mounts of Retinas from Rats 5 Days after Laser Induction of Choroidal Neovascularization.

Figure 28A:
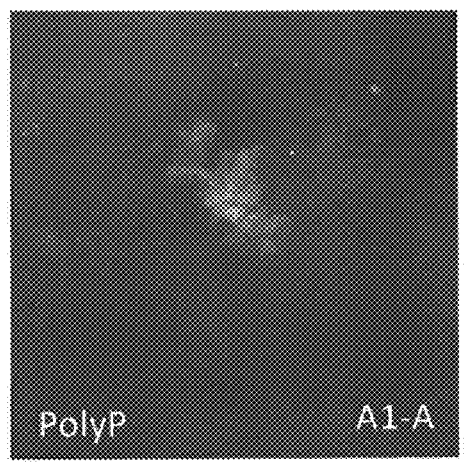
FIGS. 28A-D are photographs of whole mounts of retinas from rats after laser induction of choroidal neovascularization. A,B: polyphosphate (PolyP$_{>1000}$) (final estimated concentration of 200 μM); C,D: P$_1$. Post-fixation staining for vascular endothelium (green) and membrane attack complex (MAC) (red). Merged images are shown, all at same magnification.
Figure 28B:
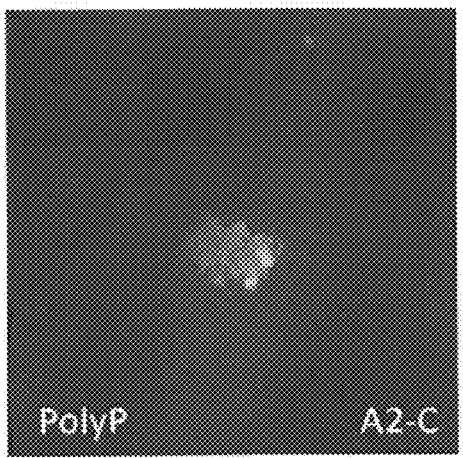
Figure 28C:
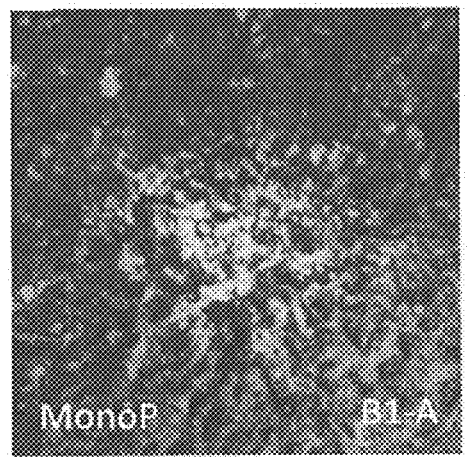
Figure 28D:
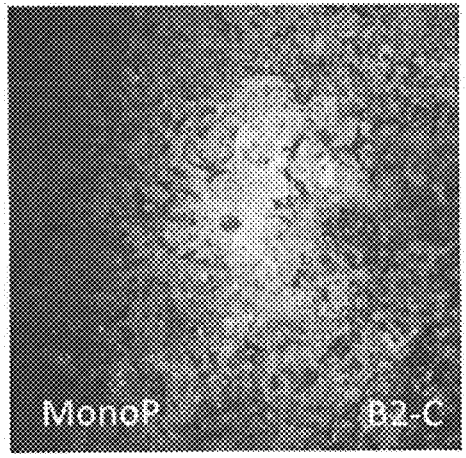

Rats were all treated 10' after laser with intravitreal injection of either polyphosphate (PolyP$_{>1000}$) (final estimated concentration of 200 μM) or P$_1$ (FIGS. 28A-D). FIGS. 28A, B: polyphosphate (PolyP$_{>1000}$) (final estimated concentration of 200 μM); FIGS. 28C, D: P$_1$. Post-fixation staining for vascular endothelium (green) and membrane attack complex (MAC) (red). Merged images are shown, all at same magnification. Results indicate that polyphosphate (PolyP$_{>1000}$) prevents neovascularization and deposition of MAC on retina after laser injury, whereas monophosphate (P$_1$) is not protective.

REFERENCES

1. Harold F M. Inorganic polyphosphates in biology: structure, metabolism, and function. *Bacteriol Rev.* 1966; 30(4): 772-794.
2. Caen J, Wu Q. Hageman factor, platelets and polyphosphates: early history and recent connection. *J Thromb Haemost.* 2010; 8(8):1670-1674.
3. Rao N N, Kornberg A. Inorganic polyphosphate regulates responses of *Escherichia coli* to nutritional stringencies, environmental stresses and survival in the stationary phase. *Prog Mol Subcell Biol.* 1999; 23:183-195.
4. Kornberg A, Rao N N, Ault-Riche D. Inorganic polyphosphate: a molecule of many functions. *Annu Rev Biochem.* 1999; 68:89-125.
5. Brown M R, Kornberg A. Inorganic polyphosphate in the origin and survival of species. *Proc Natl Acad Sci USA.* 2004; 101(46):16085-16087.
6. Brown M R, Kornberg A. The long and short of it-polyphosphate, PPK and bacterial survival. *Trends Biochem Sci.* 2008; 33(6):284-290.
7. Ruiz F A, Lea C R, Oldfield E, Docampo R. Human platelet dense granules contain polyphosphate and are similar to acidocalcisomes of bacteria and unicellular eukaryotes. *J Biol Chem.* 2004; 279(43):44250-44257.
8. Muller F, Mutch N J, Schenk W A, et al. Platelet polyphosphates are proinflammatory and procoagulant mediators in vivo. *Cell.* 2009; 139(6):1143-1156.
9. Smith S A, Mutch N J, Baskar D, Rohloff P, Docampo R, Morrissey J H. Polyphosphate modulates blood coagulation and fibrinolysis. *Proc Natl Acad Sci USA.* 2006; 103(4):903-908.
10. Bae J S, Lee W, Rezaie A R. Polyphosphate elicits proinflammatory responses that are counteracted by activated protein C in both cellular and animal models. *J Thromb Haemost.* 2012; 10(6):1145-1151.
11. Muller F, Renne T. Platelet polyphosphates: the nexus of primary and secondary hemostasis. *Scand J Clin Lab Invest.* 2011; 71(2):82-86.
12. Mutch N J, Engel R, Uitte de Willige S, Philippou H, Ariens R A. Polyphosphate modifies the fibrin network and down-regulates fibrinolysis by attenuating binding of tPA and plasminogen to fibrin. *Blood.* 2010; 115(19):3980-3988.
13. Mutch N J, Myles T, Leung L L, Morrissey J H. Polyphosphate binds with high affinity to exosite II of thrombin. *J Thromb Haemost.* 2010; 8(3):548-555.
14. Smith S A, Choi S H, Davis-Harrison R, et al. Polyphosphate exerts differential effects on blood clotting, depending on polymer size. *Blood.* 2010; 116(20):4353-4359.
15. Smith S A, Morrissey J H. Polyphosphate as a general procoagulant agent. *J Thromb Haemost.* 2008; 6(10):1750-1756.
16. Smith S A, Morrissey J H. Polyphosphate enhances fibrin clot structure. *Blood.* 2008; 112(7):2810-2816.
17. van der Meijden P E, Heemskerk J W. Polyphosphates: a link between platelet activation, intrinsic coagulation and inflammation? *Expert Rev Hematol.* 2010; 3(3):269-272.
18. Morgan B P. The complement system: an overview. *Methods Mol Biol.* 2000; 150:61-71.
19. Ricklin D, Lambris J D. Complement-targeted therapeutics. *Nat Biotechnol.* 2007; 25(11):1265-1275.
20. Del Conde I, Cruz M A, Zhang H, Lopez J A, Afshar-Kharghan V. Platelet activation leads to activation and propagation of the complement system. *J Exp Med.* 2005; 201(6):871-879.
21. Hadders M A, Bubeck D, Roversi P, et al. Assembly and regulation of the membrane attack complex based on structures of C5b6 and sC5b9. *Cell Rep.* 2012; 1(3):200-207.
22. Delvaeye M, Conway E M. Coagulation and innate immune responses: can we view them separately? *Blood.* 2009; 114(2):2367-2374.
23. Xu J, Lupu F, Esmon C T. Inflammation, innate immunity and blood coagulation. *Hamostaseologie.* 2010; 30(1):5-6, 8-9.
24. Weiler H. Regulation of inflammation by the protein C system. *Crit Care Med.* 2010; 38(2 Suppl):S18-25.
25. Rezaie A R. Regulation of the Protein C Anticoagulant and Antiinflammatory Pathways. *Curr Med Chem.* 2010; 17(19):2059-2069.
26. Oehmcke S, Herwald H. Contact system activation in severe infectious diseases. *J Mol Med.* 2010; 88(2):121-126.
27. Luyendyk J P, Sullivan B P, Guo G L, Wang R. Tissue factor-deficiency and protease activated receptor-1-deficiency reduce inflammation elicited by diet-induced steatohepatitis in mice. *Am J Pathol.* 2010; 176(1):177-186.
28. La Bonte L R, Pavlov V I, Tan Y S, et al. Mannose-binding lectin-associated serine protease-1 is a significant contributor to coagulation in a murine model of occlusive thrombosis. *J Immunol.* 2012; 188(2):885-891.
29. Takahashi K, Chang W C, Takahashi M, et al. Mannose-binding lectin and its associated proteases (MASPs) mediate coagulation and its deficiency is a risk factor in developing complications from infection, including disseminated intravascular coagulation. *Immunobiology.* 2011; 216(1-2):96-102.
30. Zeerleder S. C1-inhibitor: more than a serine protease inhibitor. *Semin Thromb Hemost.* 2011; 37(4):362-374.
31. Krisinger M J, Goebeler V, Lu Z, et al. Thrombin generates previously unidentified C5 products that support the terminal complement activation pathway. *Blood.* 2012; 120(8):1717-1725.
32. Girardi G, Mackman N. Tissue factor in antiphospholipid antibody-induced pregnancy loss: a pro-inflammatory molecule. *Lupus.* 2008; 17(10):931-936.
33. Krarup A, Wallis R, Presanis J S, Gal P, Sim R B. Simultaneous activation of complement and coagulation by MBL-associated serine protease 2. *PLoS ONE.* 2007; 2(7): e623.
34. Yin W, Ghebrehiwet B, Peerschke E I. Expression of complement components and inhibitors on platelet microparticles. *Platelets.* 2008; 19(3):225-233.
35. Zhang Q, Li Y, Tang C M. The role of the exopolyphosphatase PPX in avoidance by *Neisseria meningitidis* of complement-mediated killing. *J Biol Chem.* 2010; 285(44):34259-34268.
36. Kimura A, Ikeo K, Nonaka M. Evolutionary origin of the vertebrate blood complement and coagulation systems inferred from liver EST analysis of lamprey. *Dev Comp Immunol.* 2009; 33(1):77-87.

37. Rawal N, Pangburn M K. C5 convertase of the alternative pathway of complement. Kinetic analysis of the free and surface-bound forms of the enzyme. *J Biol Chem.* 1998; 273(27):16828-16835.
38. Niesen F H, Berglund H, Vedadi M. The use of differential scanning fluorimetry to detect ligand interactions that promote protein stability. *Nat Protoc.* 2007; 2(9):2212-2221.
39. Lorenz B, Schroder H C. Mammalian intestinal alkaline phosphatase acts as highly active exopolyphosphatase. *Biochim Biophys Acta.* 2001; 1547(2):254-261.
40. Lachmann P J, Thompson R A. Reactive lysis: the complement-mediated lysis of unsensitized cells. II. The characterization of activated reactor as C56 and the participation of C8 and C9. *J Exp Med.* 1970; 131(4):643-657.
41. Tinsley C R, Gotschlich E C. Cloning and characterization of the meningococcal polyphosphate kinase gene: production of polyphosphate synthesis mutants. *Infect Immun.* 1995; 63(5):1624-1630.
42. Di Cera E. Thrombin as procoagulant and anticoagulant. *J Thromb Haemost.* 2007; 5 Suppl 1:196-202.
43. Lechtenberg B C, Freund S M, Huntington J A. An ensemble view of thrombin allostery. *Biol Chem.* 2012; 393(9):889-898.
44. Drake W T, Lopes N N, Fenton J Wn, lssekutz A C. Thrombin enhancement of interleukin-1 and tumor necrosis factor-alpha induced polymorphonuclear leukocyte migration. *Lab Invest.* 1992; 67(5):617-627.
45. Fujita T, Yamabe H, Shimada M, et al. Thrombin enhances the production of monocyte chemoattractant protein-1 and macrophage inflammatory protein-2 in cultured rat glomerular epithelial cells. *Nephrol Dial Transplant.* 2008; 23(11):3412-3417.
46. Wadgaonkar R, Somnay K, Garcia J G. Thrombin induced secretion of macrophage migration inhibitory factor (MIF) and its effect on nuclear signaling in endothelium. *J Cell Biochem.* 2008; 105(5):1279-1288.
47. Huber-Lang M, Sarma J V, Zetoune F S, et al. Generation of C5a in the absence of C3: a new complement activation pathway. *Nat Med.* 2006; 12(6):682-687.
48. Bae J S, Kim Y U, Park M K, Rezaie A R. Concentration dependent dual effect of thrombin in endothelial cells via Par-1 and Pi3 Kinase. *J Cell Physiol.* 2009; 219(3):744-751.
49. Morser J. Thrombomodulin links coagulation to inflammation and immunity. *Curr Drug Targets.* 2012; 13(3): 421-431.
50. Lorenz B, Leuck J, Kohl D, Muller W E, Schroder H C. Anti-HIV-1 activity of inorganic polyphosphates. *J Acquir Immune Defic Syndr Hum Retrovirol.* 1997; 14(2):110-118.
51. Rondina M T, Weyrich A S, Zimmerman G A. Platelets as cellular effectors of inflammation in vascular diseases. *Circ Res.* 2013; 112(11):1506-1519.
52. Schmaier A H, Amenta S, Xiong T, Heda G D, Gewirtz A M. Expression of platelet 1 inhibitor. *Blood.* 1993; 82(2): 465-474.
53. Wiedmer T, Esmon C T, Sims P J. Complement proteins C5b-9 stimulate procoagulant activity through platelet prothrombinase. *Blood.* 1986; 68(4):875-880.
54. Licht C, Pluthero F G, Li L, et al. Platelet-associated complement factor H in healthy persons and patients with atypical HUS. *Blood.* 2009; 114(20):4538-4545.
55. Gunay-Aygun M, Huizing M, Gahl W A. Molecular defects that affect platelet dense granules. *Semin Thromb Hemost.* 2004; 30(5):537-547.
56. Nurden A, Nurden P. Advances in our understanding of the molecular basis of disorders of platelet function. *J Thromb Haemost.* 2011; 9 Suppl 1:76-91.
57. Hurford M T, Sebastiano C. Hermansky-pudlak syndrome: report of a case and review of the literature. *Int J Clin Exp Pathol.* 2008; 1(6):550-554.
58. Kaplan J, De Domenico I, Ward D M. Chediak-Higashi syndrome. *Curr Opin Hematol.* 2008; 15(1):22-29.
59. Docampo R, Moreno S N. Acidocalcisomes. *Cell Calcium.* 2011; 50(2):113-119.
60. Ninomiya H, Sims P J. The human complement regulatory protein CD59 binds to the alpha-chain of C8 and to the "b"domain of C9. *J Biol Chem.* 1992; 267(19):13675-13680.
61. Risitano A M. Paroxysmal nocturnal hemoglobinuria and the complement system: recent insights and novel anti-complement strategies. *Adv Exp Med Biol.* 2013; 735:155-172.
62. Tschopp J, Chonn A, Hertig S, French L E. Clusterin, the human apolipoprotein and complement inhibitor, binds to complement C7, C8 beta, and the b domain of C9. *J Immunol.* 1993; 151(4):2159-2165.
63. Falgarone G, Chiocchia G. Chapter 8: Clusterin: A multifacet protein at the crossroad of inflammation and autoimmunity. *Adv Cancer Res.* 2009; 104:139-170.
64. Podack E R, Kolb W P, Muller-Eberhard H J. The SC5b-7 complex: formation, isolation, properties, and subunit composition. *J Immunol.* 1977; 119(6):2024-2029.
65. Hobart M J, Fernie B A, Wurzner R, et al. Difficulties in the ascertainment of C9 deficiency: lessons to be drawn from a compound heterozygote C9-deficient subject. *Clin Exp Immunol.* 1997; 108(3):500-506.
66. Jessen T E, Barkholt V, Welinder K G. A simple alternative pathway for hemolytic assay of human complement component C3 using methylamine-treated plasma. *J Immunol Methods.* 1983; 60(1-2):89-100.
67. van den Berg C W, Morgan B P. Complement-inhibiting activities of human CD59 and analogues from rat, sheep, and pig are not homologously restricted. *J Immunol.* 1994; 152(8):4095-4101.
68. Smith S A, Morrissey J H. Sensitive fluorescence detection of polyphosphate in polyacrylamide gels using 4',6-diamidino-2-phenylindol. *Electrophoresis.* 2007; 28(19): 3461-3465.
69. Wat J, Foley J H, Krisinger M J, Ocariza L M, Lei V, Wasney G, Lameignere E, Strynadka N C, Smith S A, Morrissey J H, Conway E M. Polyphosphate suppresses complement via the terminal pathway. *Blood.* 2014; 123: 768-76.
70. Beinrohr L, Murray-Rust T A, Dyksterhuis L, Zavodszky P, Gal P, Pike R N, Wijeyewickrema L C. Serpins and the complement system. *Methods in enzymology.* 2011; 499: 55-75.
71. Bos I G, Hack C E, Abrahams J P. Structural and functional aspects of C1-inhibitor. *Immunobiology.* 2002; 205: 518-33.
72. Murray-Rust T A, Kerr F K, Thomas A R, Wu T, Yongqing T, Ong P C, Quinsey N S, Whisstock J C, Wagenaar-Bos I C, Freeman C, Pike R N. Modulation of the proteolytic activity of the complement protease C1s by polyanions: implications for polyanion-mediated acceleration of interaction between C1s and SERPING1. *Biochem J.* 2009; 422: 295-303.
73. Du S, Wang S, Wu Q, Hu J, Li T. Decorin inhibits angiogenic potential of choroid-retinal endothelial cells by downregulating hypoxia-induced Met, Rac1, HIF-1alpha and VEGF expression in cocultured retinal pigment epithelial cells. *Experimental eye research.* 2013; 116: 151-60.
74. Dunn K C, Aotaki-Keen A E, Putkey F R, Hjelmeland L M. ARPE-19, a human retinal pigment epithelial cell line with differentiated properties. *Experimental eye research.* 1996; 62: 155-69.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method for inhibiting complement activation, comprising administering an effective amount of an inorganic polyphosphate to a subject in need thereof, or by applying a polyphosphate to a surface of an organ or biomaterial, wherein the polyphosphate comprises at least 10 phosphate units and wherein the polyphosphate inhibits complement activation by one or more of: binding to the C6 complement protein, C1-esterase inhibitor (C1-inh), factor H or factor B; enhancing the activity of C1-inh; interfering with C1s-mediated cleavage of C2; destabilizing the C5b-6 complement protein complex; interfering with C5b,6 interaction with C7; interfering with binding of C5b-7 to a cell membrane; interfering with integration of C5b-7 into a cell membrane; interfering with binding of C5b-8 to a cell membrane; interfering with integration of C5b-8 into a cell membrane; destabilizing the membrane attack complex (MAC); or reducing the amount of C5b-9 deposited on a cell surface.

2. The method of claim 1 wherein the polyphosphate reduces hemolysis.

3. The method of claim 1 wherein the surface is a biomaterial.

4. The method of claim 3 wherein the biomaterial is exposed to blood or blood products in the body or outside of the body.

5. The method of claim 3 wherein the biomaterial is a medical device, stent vascular graft, heart valve, blood product storage container or bag, or dialysis or filtration device.

6. The method of claim 1 wherein the polyphosphate is applied to the organ prior to transplantation of the organ.

* * * * *